(12) United States Patent
Martin et al.

(10) Patent No.: US 11,613,722 B2
(45) Date of Patent: Mar. 28, 2023

(54) PERFUSION BIOREACTOR PLATFORM

(71) Applicant: Corning Incorporated, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 15/498,062

(22) Filed: Apr. 26, 2017

(65) Prior Publication Data
US 2017/0306281 A1     Oct. 26, 2017

Related U.S. Application Data

(63) Continuation of application No. PCT/US2015/058032, filed on Oct. 29, 2015.
(Continued)

(51) Int. Cl.
*C12M 1/00* (2006.01)
*C12M 1/14* (2006.01)
(Continued)

(52) U.S. Cl.
CPC .............. *C12M 23/12* (2013.01); *C12M 1/14* (2013.01); *C12M 3/04* (2013.01); *C12M 23/16* (2013.01);
(Continued)

(58) Field of Classification Search
CPC ............ C12M 1/00; C12M 1/14; C12M 3/00; C12M 3/04; C12M 23/12; C12M 23/16; C12M 25/14; C12M 29/10
(Continued)

(56) References Cited

U.S. PATENT DOCUMENTS 2,947,116 A     8/1960   Wilton et al.
3,630,849 A    12/1971   David et al.
(Continued)

FOREIGN PATENT DOCUMENTS

AU     2004256209 A1     1/2005
CA        2558946 A1     1/2005
(Continued)

OTHER PUBLICATIONS

Achilli; "Advances in the Formation, Use and Understanding of Muli-Cellular Spheroids", Expert Opin. Biol. Ther. (2012) 12 (10) 1347-1360.
(Continued)

*Primary Examiner* — Liban M Hassan
(74) *Attorney, Agent, or Firm* — Michael G. Panian

(57) ABSTRACT

A cell culture apparatus includes one or more plates having a first major surface and an opposing second major surface. The first major surface comprises a structured surface defining a plurality of wells. Each well has an interior surface defining an upper aperture and a nadir, wherein the upper aperture of each well has a diametric dimension in a range from 100 micrometers to 2000 micrometers. The apparatus also includes a plurality of spacers extending from the first major surface along a length of the bottom surface. A plurality of flow channels are defined between adjacent rails.

16 Claims, 20 Drawing Sheets

Related U.S. Application Data

(60) Provisional application No. 62/072,039, filed on Oct. 29, 2014.

(51) Int. Cl.
  *C12M 3/00* (2006.01)
  *C12M 1/32* (2006.01)
  *C12M 3/06* (2006.01)
  *C12M 3/04* (2006.01)
  *C12M 1/12* (2006.01)

(52) U.S. Cl.
  CPC ............ *C12M 25/14* (2013.01); *C12M 29/10* (2013.01); *C12M 1/00* (2013.01); *C12M 3/00* (2013.01)

(58) Field of Classification Search
  USPC ...................................................... 435/289.1
  See application file for complete search history.

(56) References Cited

U.S. PATENT DOCUMENTS

| | | |
|---|---|---|
| 4,670,396 A | 6/1987 | Bear et al. |
| 4,927,764 A | 5/1990 | Lyman et al. |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A * | 8/1993 | Berry .................... C12M 23/34 435/294.1 |
| 5,272,084 A | 12/1993 | O'Connell et al. |
| 5,319,436 A | 6/1994 | Manns et al. |
| 5,374,557 A | 12/1994 | Verma |
| 5,487,872 A | 1/1996 | Hafeman et al. |
| 5,554,536 A | 9/1996 | Rising |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,759,494 A | 6/1998 | Szlosek |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 * | 6/2010 | Martin .................... C12M 23/04 435/294.1 |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 11,441,121 B2 | 9/2022 | Bennett et al. |
| 2002/0022219 A1 | 2/2002 | Clements et al. |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader et al. |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2005/0032208 A1 | 2/2005 | Oh et al. |
| 2005/0047971 A1 | 3/2005 | Clements et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 * | 8/2007 | Li .......................... C12M 23/12 435/4 |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0299649 A1 | 12/2008 | Martin et al. |
| 2008/0300278 A1 | 12/2008 | Torrens Jover et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 * | 12/2009 | Cattadoris ........... B29C 45/0053 435/294.1 |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Mueller |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |

(56) References Cited

U.S. PATENT DOCUMENTS

| | | | |
|---|---|---|---|
| 2011/0086375 A1 | 4/2011 | Ungrin et al. | |
| 2011/0097790 A1 | 4/2011 | Yerbic | |
| 2011/0129923 A1 | 6/2011 | Wilson et al. | |
| 2012/0064627 A1 | 3/2012 | Khine et al. | |
| 2012/0129208 A1 | 5/2012 | Khine et al. | |
| 2012/0129257 A1* | 5/2012 | Yu .................. | C12M 23/44 |
| | | | 435/395 |
| 2012/0219572 A1 | 8/2012 | Prockop et al. | |
| 2013/0122539 A1 | 5/2013 | Li et al. | |
| 2013/0122580 A1 | 5/2013 | Tsukada et al. | |
| 2013/0143254 A1 | 6/2013 | Thomas et al. | |
| 2013/0164848 A1* | 6/2013 | Munaka ............ | C12M 23/12 |
| | | | 435/383 |
| 2013/0203159 A1 | 8/2013 | Itoh et al. | |
| 2013/0344598 A1 | 12/2013 | Nistor | |
| 2014/0004086 A1 | 1/2014 | Peak | |
| 2014/0099717 A1 | 4/2014 | Fraker et al. | |
| 2014/0106394 A1 | 4/2014 | Ko et al. | |
| 2014/0106452 A1 | 4/2014 | Vukasinovic | |
| 2014/0120573 A1 | 5/2014 | Tavana et al. | |
| 2014/0178992 A1 | 6/2014 | Nakashima et al. | |
| 2014/0221225 A1 | 8/2014 | Danen et al. | |
| 2014/0227784 A1 | 8/2014 | Ejiri et al. | |
| 2014/0315296 A1 | 10/2014 | Wilson | |
| 2014/0322806 A1 | 10/2014 | Bennett et al. | |
| 2015/0004686 A1 | 1/2015 | Goral et al. | |
| 2015/0064738 A1 | 3/2015 | Tsukada et al. | |
| 2015/0072405 A1 | 3/2015 | Ito | |
| 2015/0184119 A1 | 7/2015 | Tsukada et al. | |
| 2015/0247112 A1 | 9/2015 | Orr et al. | |
| 2016/0003796 A1 | 1/2016 | Kranbuehl | |
| 2016/0017267 A1 | 1/2016 | Hansen et al. | |
| 2016/0137962 A1 | 5/2016 | Ejiri et al. | |
| 2016/0194588 A1 | 7/2016 | Guenat et al. | |
| 2016/0216250 A1 | 7/2016 | Ritter et al. | |
| 2017/0073625 A1 | 3/2017 | Kasuto et al. | |
| 2017/0226455 A1 | 8/2017 | Fang et al. | |
| 2017/0283757 A1 | 10/2017 | Carter et al. | |
| 2017/0306281 A1 | 10/2017 | Martin et al. | |
| 2017/0342363 A1 | 11/2017 | Fang et al. | |
| 2018/0201888 A1 | 7/2018 | Miwa et al. | |
| 2020/0239854 A1 | 7/2020 | Ayano et al. | |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1234112 A | 11/1999 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 0307048 A2 | 9/1988 |
| EP | 0605527 A1 | 7/1994 |
| EP | 0681846 A2 | 11/1995 |
| EP | 0800571 A2 | 10/1997 |
| EP | 0834552 A1 | 4/1998 |
| EP | 0965633 A1 | 12/1999 |
| EP | 1181349 A1 | 2/2002 |
| EP | 1445022 B1 | 10/2006 |
| EP | 1348533 B1 | 11/2006 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 06327462 A | 11/1994 |
| JP | 09173049 A | 7/1997 |
| JP | 09-234811 A | 9/1997 |
| JP | 10-210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004-129558 A | 4/2004 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-542230 A | 12/2009 |
| JP | 2010088347 A | 4/2010 |
| JP | 2010-104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2012249547 A | 12/2012 |
| JP | 2013-055911 A | 3/2013 |
| JP | 2014132869 A | 7/2014 |
| JP | 2015-012827 A | 1/2015 |
| JP | 2015073520 A | 4/2015 |
| JP | 5845185 B2 | 1/2016 |
| JP | 2016-136921 A | 8/2016 |
| JP | 2017-532970 A | 11/2017 |
| KR | 2014113139 A | 9/2014 |
| KR | 10-2014-0125662 A | 10/2014 |
| WO | 1992007063 A2 | 4/1992 |
| WO | 93/07258 A1 | 4/1993 |
| WO | 96/21851 A2 | 7/1996 |
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008/118500 A1 | 10/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2012036011 A1 | 3/2012 |
| WO | 2012/170232 A1 | 12/2012 |

(56) References Cited

FOREIGN PATENT DOCUMENTS

| | | |
|---|---|---|
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015/033507 A1 | 3/2015 |
| WO | 2015/061907 A1 | 5/2015 |
| WO | 2014072432 A1 | 5/2015 |
| WO | 2016/064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2017025584 A1 | 2/2017 |
| WO | 2017/047735 A1 | 3/2017 |
| WO | 2017/077163 A1 | 5/2017 |
| WO | 2017/142410 A1 | 8/2017 |
| WO | 2018/200893 A1 | 11/2018 |
| WO | 2019/014621 A1 | 1/2019 |
| WO | 2019/014627 A1 | 1/2019 |
| WO | 2019/014635 A1 | 1/2019 |
| WO | 2019/014636 A1 | 1/2019 |
| WO | 2019/178039 A1 | 9/2019 |

OTHER PUBLICATIONS

Alepee et al. "State of the art 3D cultures (organs-on-a-chip) in safety testing and pathophysiology" Trnasatlantic Think Tank for Toxicology, t4 Workshop Report, Altex 31 4/14, pp. 441-477, retrieved from: http://dx.doi.org/10.14573/altex1406111 (Jul. 14, 2014).

Anada et al; "An Oxygen-Permeable Spheroid Culture System for the Prevention of Central Hypdxia and Necrosis of Spheroids"; Biomaterials, 33, (2012) 8430-8441.

Bartosh et al; "Aggregation of Human Mesenchymal Stromal Cells (MSCS) Into 3D Spheroid Enhances Their Antiinflammatory Properties"; PNAS, Aug. 3, 2010, vol. 107, No. 31 pp. 13724-13729.

Carver et al; "Multicellular Tumor Spheroids as a Model for Assessing Delivery of Oligonucleotides in Three Dimensions"; Molecular Therapy—Nucleic Acids (2014) 3, E153; 8 Pages.

Chen et al. "Microfluidic array for 3-dimensional perfusion culture of human mammary epithelial cells", Biomedical Microdevices (2011) vol. 13, issue 4. p. 753-758.

Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.

Dolznig and Walzl, "Organotypic spheroid cultures to study tumor-stroma interactions during cancer development." Drug discovery today, V 8., No. 2-3, 2011, 113-118.

Engelberg and Ropella, "Essential operating principles for tumor spheroid growth." BMC Systems Biology 2008, 2, 110.

Friedrich et al. "Spheroid-based drug screen: considerations and practical approach." Nature protocols, 2009, vol. 4 No. 3, 309-323.

Friedrich et al: "Experimental anti-tumor therapy in 3-D: spheroids—old hat or new challenge?" Int J Radiat Biol 2007, 83:849-871.

Frith et al. "Dynamic three-dimensional culture methods enhance mesenchymal stem cell properties and increase therapeutic potential." Tissue engineering, 2010, 16, No. 4, 735-749.

Fukuda et al. "Efficacy of a polyurethane foam/spheroid artificial liver using human hepatoblastoma cell line (HepG2)." Cell Transplant 2003;12:51-8.

G-Plate: Accelerate your cell cultures to the next dimension, "An original cell culture model allowing for inland shaped 3D cell aggregates" 1 page, retrieved Sep. 8, 2015.

Haycock. "3D cell culture: a review of current approaches and techniques." Methods Mol Biol. 2011;695:1-15.

Hirschhaeuser et al., "Mulicellular tumor spheroids: An underestimated tool is catching up again." Journal of Biotechnology, 2010, 148, 3-15.

Howes et al; "3-Dimensional Culture Systems for Anit-Cancer Compound Profiling and High-Throughput Screening Reveal Increases in EGFR Inhibitor-Mediated Cytotoxicity Compared to Monolayer Culture Systems"; PLOS One; Sep. 2004, vol. 9, Issue 9, 11 Pages.

Hribar et al; "Nonlinear 3D Projection Printing of Concave Hydrogel Microstructures for Long-Term Multicellular Spheroid and Embryoid Body Culture"; Lab Chip, 2015, 15, 2412-2418.

Hwang et al; "Microwell-Mediated Control of Embryoid Body Size Regulates Embryonic Stem Cell Fate via Differential Expression of WNT5A and WNT11"; PNAS; Oct. 6, 2009, vol. 106, No. 40, pp. 16978-16983.

Kelm et al. "Method for generation of homogeneous multicellular tumor spheroids applicable to a wide variety of cell types." Biotechnol Bioeng 2003;83:173-80.

Koide et al. "Formation of multicellular spheroids composed of adult rat hepatocytes in dish with positively charged surfaces and under other nonadherent environments." Exp Cell Res 1990;186: 227-35.

Kunz-Schughart et al: "The use of 3-D cultures for high-throughput screening: the multicellular spheroid model." J Biomol Screen 2004, 9:273-285.

Kutsuzawa et al; "Highly Robust Protein Production by Co-Culture of CHO Spheroids Layared on Feeder Cells in Serum-Free Medium"; Colloid Polym Sci (2014) 292; 839-848.

Labusca et al. "Scaffold-free culture of mesenchymal stem cell spheroids in suspension preserves multilineage potential", Cell Tissue Res. Mar. 2012 ; 347(3): 701-711.

Landry et al. "Spheroidal aggregate culture of rat liver cell: histotypic reorganization, biomatrix deposition, and maintenance of functional activities." J Cell Biol 1985;101:914-23.

Lau et al., "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.

Liu et al. "Quasi-spherical microwells on superhydrophobic substrates for long term culture of multicellular spheroids and high throughput assays" Biomaterials and Cancer 35 (2014) pp. 6060-6068.

Liu et al; "Advanced Micromachining of Concave Microwells for Long Term On-Chip Culture of Multicellular Tumour Spheroids", ACS Appl. Mater. Interfaces, 2014, 35 Pages.

Lu et al. "Galactosylated PVDF membrane promotes hepatocyte attachment and functional maintenance." Biomaterials 2003;24:4893-903.

Madoux et al; "Building Phenotypic 3D Spheroid HTS Assays to Identify Synthetic Lethal Small Molecule Inhibitors of KRAS"; The Scripps Research Institute Molecular Screening Center and Department of Cancer Biology, Scripps Florida, Jupiter, Florida, Department of Pathology, Jupiter Medical Center, Jupiter, Florida.

Markovitz-Bishitz, "A polymer microstructure array for the formation, culturing, and high throughput drug screening of breast cancer spheroids" Biomaterials and Biotechnology 31 (2010) pp. 8436-8444.

Messner et al., Multi-cell type human liver microtissues for hepatotoxicity testing. Archives of Toxicology Nov. 11, 2012.

Mironov et al; "Organ Printing: Tissue Spheroids as Buliding Blocks" Biomaterials, 2009; 30 (12) 2164-2174.

Moon et al; "Optimizing Human Embryonic Stem Cells Differentiation Efficiency by Screening Size-Tunable Homogenous Embryoid Bodies"; Biomaterials; 35 (2014) 5987-5997.

Murphy et al; "3D Bioprinting of Tissues and Organs"; Nature Biotechnology, vol. 32, No. 8, Aug. 2014, pp. 773-785.

Otsuka et al. "Two-dimensional multiarray formation of hepatocyte spheroids on a microfabricated PEG-brush surface." Chembiochem 2004;5:850-5.

Peshwa et al. "Mechanistics of formation and ultrastructural evaluation of hepatocyte spheroids." In Vitro Cell Dev Biol Anim 1996;32:197-203.

(56) References Cited

OTHER PUBLICATIONS

Rezende et al; Scalable Biofabrication of Tissue Spheroids for Organ Printing; Sciverse Science Direct, Porcedia Cirp 5, (2013) 276-281.
Sa et al. "Round-bottomed Honeycomb Microwells: Embryoid body shape correlates with stem cell fate" Journal of Developmental Biology and Tissue Engineering vol. 4(2), pp. 12-22, May 2012.
Sakai et al. "Large-scale preparation and function of porcine hepatocyte spheroids." Int J Artif Organs 1996;19:294-301.
Sakai et al; "Detachably Assembled Microfluidic Device for Perfusion Culture and Post-Culture Analysis of Spheroid Array"; Biotechnol. J. 2014, 9, 971-979.
Sakai et al; "Technique for the Control of Spheroid Diameter Using Microfabricated Chips"; Sciencedirect, Acta Biomaterials 3 (2007) 1033-1040.
Sart et al. "Three-dimensional aggregates of mesenchymal stem cells: cellular mechanisms, biological properties and applications." Tissue engineering, 2013, Part B, 00, No. 00, 1-16.
Seldon et al; "Evaluation of Encapsulated Liver Cell Spheroids in a Fluidised-Bed Bioartificial Liver for Treatment of Ischaemic Acute Liver Failure in Pigs in the Translational Setting"; PLOS One; Dec. 2013, vol. 8, Issue 12, 12 Pages.
Stemcell Technologies, Reproducible and Uniform Embryoid Bodies Using AggreWell Plates, StemCell Technologies, Version 3.0.0, Mar. 2011, Catalog #29146, pp. 1-28.
Takezawa et al. "Morphological and immunocytochemical characterization of a heterospheroid composed of fibroblasts and hepatocytes." J Cell Sci 1992;101:495-501.
Tobe et al. "Receptor-mediated formation of multilayer aggregation of primary rat hepatocytes on lactose-substituted polystyrene." Biochem Biophys Res Commun 1992;184:225-30.
Tong et al. "Long-term culture of adult rat hepatocyte spheroids." Exp Cell Res 1992;200:326-32.
Truckemüller, et al., "Thermoforming of Film-Based Biomedical Microdevices, Adv. Mater. 2011, 23, pp. 1311-1329.
Tung et al. "High-throughput 3D spheroid culture and drug testing using 384 hanging drop array." Analyst, 2011, 136, 473-478.
Uchida et al; "An Injectable Spheroid System With Genetic Modification for Cell Transplantation Therapy"; Biomaterials, 35 (2014) 2499-2506.
Urich et al; "Multicellular Self-Assembled Spheroidal Model of the Blood Brain Barrier"; Scientific Reports, 3, 1500, 8 Pages.
Vinci et al. Advances in establishment and analysis of three-dimensional tumor spheroid-based functional assays for target validation and drug evaluation, BMC Biology 2012, 10:29.
Weegman et al; "Nutrient Regulation by Continuous Feeding Removes Limitation on Cell Yeild in the Large-Scale Expansion of Mamalian Cell Spheroids"; PLOS One; Oct. 2013, vol. 8, Issue 10, 10 Pages.
Xu et al. "Characterization of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-11.
Yamada et al. "Efficient induction of hepatocyte spheroids in a suspension culture using a water-soluble synthetic polymer as an artificial matrix." J Biochem 1998;123: 1017-23.
Endo et al., Drug Deliv. and Transl. Res., 2012, vol. 2, p. 398-405.
Japanese Patent Application No. 2017523433; Machine Translation of the Office Action dated Sep. 4, 2019; Japan Patent Office; 7 Pgs.
Aline, "We Engineer Microfluidic Products"; 7 Pages; (2020) https://alineinc.com/.
CN-Bio, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5):139-149.
Corning Life Sciences Product Portfolio; 5 Pages Saved Mar. 6, 2020.
Corning(Registered) HTS Transwell(Registered)-96 Tissue Culture Systems, Permeable Supports for High Throughput Screening Applications; 2 Pages (2004).

Domansky et al, "Perfused Multiwell Plate For 30 Liver Tissue Engineering", Lab Chip, 2010, 10:51-58.
Elveflow; "Microfluidics Innovation Center"; 6 Pages; (Downloaded Mar. 9, 2020) https://www.elveflow.com.
Emulate, 6 Pages; (2019) https://emulatebio.com/.
GeoCHEM Incorporated, Product Line; hllps://www.geocheminc.com, 4 Pages; (2020).
HμREL (Registered) Corporation, Bioanalytic Tools Company; 2 Pages; (2013); http://hurelcorp.com/.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kim et al, "Shear Stress Induced By an Interstitial Level of Slow Flow Increases the Osteogenic Differentiation of Mesenchymal Stem Cells Through TAZ Activation" PLoS One, Mar. 21, 2014; 9(3), e92427, 9 pages.
Labusca, "Scaffold free 3D culture of mesenchymal stem cells; implications for regenerative medicine", J Transplant Stem Cel Biol 2015 2(1): 8.
Liquid Surge Control, LLC; "The Latest in Drop-In Baffle Technology"; 2 Pages; (2019).
Lovett et al. "Vascularization Strategies for Tissue Engineering" Tissue Engineering Part B, 2009, vol. 15, No. 3, pp. 353-370.
Mimetas the Organ-On-A-Chip Company; "Organ-On-A-Chip Models for Science and Pharma"; 4 Pages; (Downloaded Mar. 9, 2020); https://mimetas.com/.
Nortis; "Bridging the Gap Between in Vitro and in Vivo Research"; 16 Pages; (2015) https://www.nortisbio.com/.
Organovo, "Pioneering Bioprinted Tissues to Treat Disease"; 2 Pages; (Downloaded Mar. 9, 2020) http://organovo.com/.
Tara; "Innovating Predictive Cardiac Physiology"; 4 Pages; (2019) http://tarabiosystems.com/.
The Lab Depot(Registered) Products for Discovery Lab Supplies; Shake Flasks, 3 and 4 Baffles Product Information; 5 Pages (2019).
Tissue Dynamics; "Disruptive Drug Development"; 3 Pages; {Downloaded Mar. 9, 2020) https://www.tissuedynamics.com/.
Wikipedia, "Antiroll Tanks"; 3 Pages; Page Last Edited May 23, 2019.
AxoSIM, NerveSim BrianSim About Resources; Available on (http://axosim.com/), Accessed May 13, 2021, 6 Pages.
BioIVT Elevating Science, Hepatopac® Technology, Available at (https://bioivt.com/about/technologies/hepatopactechnology), Accessed May 13, 2021, 3 Pages.
Cheng et al, "MicroRNA-34a Targets Forkhead Box J2 to Modulate Differentiation of Endothelial Progenitor Cells in Response to Shear Stress", J Mol Cell Cardiol., vol. 74, 2014, pp. 4-12.
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Hsiao et al., "Effects of 3D Microwell Culture on Initial Fate Specification in Human Embryonic Stem Cells", Published in final edited form as AIChE J. vol. 60 No. 4, Apr. 2014, pp. 1225-1235.
Junji Fukuda et al., "Hepatocyte Spheroid Arrays Inside Microwells Connected With Microchannels", BioMicrofluidics 5, 2011, pp. 10.
Office Action and Search Report for CN 201580071454.0 dated Sep. 27, 2019; 8 pages; Chinese Patent Office.
Satoh et al, "A Pneumatic Pressure-Driven Multi-Throughput Microfluidic Circulation Culture System", Lab Chip, vol. 16, 2016, pp. 2339-2348.
Second Office Action and Search Report for CN 201580071454.0 dated Aug. 31, 2020; 8 pages.
Singapore Patent Application No. 11201703500X, Office Action dated Mar. 9, 2021; 8 pages; Singapore Patent Office.
Tissuse; Technology, Available on (https://www.tissuse.com/en/technology/), Accessed May 11, 2021, 4 pages.
Wrighton et al, "Forces of Change: Mechanics Underlying Formation of Functional 3D Organ Buds", Cell Stem Cell, vol. 16, May 7, 2015, pp. 453-454.

(56) References Cited

OTHER PUBLICATIONS

Curcio et al. "Mass transfer and metabolic reactions in hepatocyte spheroids cultured in rotating wall gas-permeable membrane system." Biomaterials 28 (2007) 5487-5497. (Year: 2007).

Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).

Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).

\* cited by examiner

PERFUSION BIOREACTOR PLATFORM

PRIORITY CLAIM

This is a continuation application of International Patent Application Serial No. PCT/US15/58032 filed on Oct. 29, 2015, which claims the benefit of priority to U.S. Provisional Application Ser. No. 62/072,039, filed on Oct. 29, 2014, the contents of which are relied upon and incorporated herein by reference in their entirety, and the benefit of priority under 35 U.S.C. § 120 is hereby claimed.

FIELD

The present disclosure relates to apparatuses, systems and methods for culturing cells.

TECHNICAL BACKGROUND

The viable cell density (VCD) that can be maintained is a primary variable driving productivity and cost in bioreactor vessels. In bioreactors one limitation to achieving the highest possible VCD is the shear force that cells experience as bags are rocked faster or impeller velocities increased to accommodate elevated nutrient and gas exchange requirements due to the high density of cells in culture. Additionally, for applications where attachment dependent cells are the product, such as for production of cells for screening, cellular therapy, or regenerative medicine applications, it can be difficult to harvest the cells from the reactor.

In recent years there have been efforts to run bioreactors in a steady state, continuously perfused mode in an effort to greatly reduce production costs while maintaining consistent quality in an automated process. Although this method has been shown to be a powerful method to maintain high cell densities, there are difficulties regarding its suitability for commercial production of therapeutic proteins. One risk is unstable expression levels after a prolonged period in culture, with cells exhibiting fastest growth potential rather than those expressing the protein of interest being selected over time.

Accordingly, new cell culture apparatuses that provide for one or more of increased stability of cells of interest, ease of harvest of attachment dependent cells, or increased viable cell density would be desirable.

BRIEF SUMMARY

In accordance with various embodiments of the present disclosure, cell culture apparatuses having one or more plates, which can be stacked, are described. The plates have a major surface defining a structured surface. The structured surface defines a plurality of wells in which cells can be cultured. The wells can have dimensions on the micrometer scale and can be configured to promote formation of spheroid cell clusters. The apparatuses described herein also have a plurality of spacers to maintain the space between stacked plates. In embodiments, such spacers include posts or spaced apart rails that extend from the major surface along the length of the plate. A plurality of flow channels are formed between adjacent plates and/or rails for perfusion of cell culture media. The structured surfaces can support very high cell density cell growth, which can be enhanced by spheroid formation. Spheroid formation should also enhance cell functional stability, as spheroids can maintain differentiated cell function indicative of a more in vivo like response relative to cells grown in a monolayer. In some embodiments, the wells in which cells are cultured are non-adherent to the cells, which can facilitate harvesting of the cells. In various embodiments described herein, the apparatuses are designed to allow for passive diffusion of metabolic gases, which can allow for lower media perfusion rates and thus subject the cultured cells to less shear.

In various embodiments, this disclosure describes a cell culture apparatus. The cell culture apparatus includes one or more plates having a first major surface and an opposing second major surface. The first major surface comprises a structured surface defining a plurality of wells. Each well has an interior surface defining an upper aperture and a nadir, wherein the upper aperture of each well has a diametric dimension in a range from 200 micrometers to 500 micrometers, or a range from 100 micrometers to 2000 micrometers. The apparatus also includes a plurality of spaced apart rails (spacers) extending from the first major surface along a length of the first major surface. A plurality of flow channels are defined between adjacent rails.

In some embodiments, provided herein are methods of producing protein (e.g., a therapeutic protein, such as a therapeutic antibody or antibody fragment), comprising: a) culturing cells expressing a protein in the wells of a cell culture apparatus as described herein; and b) isolating the protein from the cells.

In some embodiments, wells (e.g., microwells) have a cross-sectional shape approximating a sine wave. In such embodiments, the bottom of the well is rounded (e.g., hemispherically round), the side walls increase in diameter from the bottom of the well to the top and the boundary between wells is rounded. As such the top of the wells does not terminate at a right angle. In some embodiments, a well has a diameter D at the half-way point (also termed $D_{half-way}$) between the bottom and top, a diameter $D_{top}$ at the top of the well and a height H from bottom to top of the well. In these embodiments, $D_{top}$ is greater than D. Additional embodiments are shown in FIG. 15, where the width of the well is greater than the width of the barrier between contiguous wells. Such an embodiment permits a greater number of wells within a given area of a culture surface.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 17A is an illustration in cross-section.

FIG. 18A is an illustration in cross-section.

FIG. 19A is an illustration in cross-section. FIG. 19B is a top-down drawing of the exemplary embodiment of an array of wells, taken at line B-B of FIG. 19A. FIG. 19C is a drawing of an array of wells having a sinusoidal or parabolic shape.

DETAILED DESCRIPTION

Figure 1:
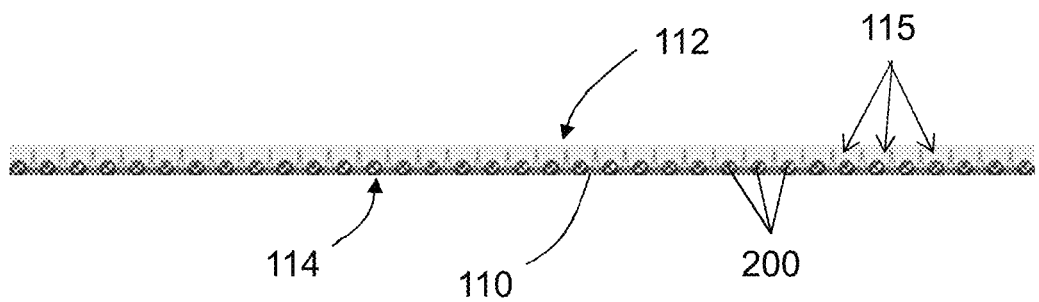
FIG. 1 is a schematic side view of an embodiment of a substrate having a structured surface having wells for culturing cells.

Reference will now be made in greater detail to various embodiments of the subject matter of the present disclosure, some embodiments of which are illustrated in the accompanying drawings. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

The present disclosure describes, among other things, cell culture apparatuses having a plurality of stacked plates, each having a first major surface and an opposing second major surface. The first major surface includes a structured surface defining a plurality of or an array of microwells. In embodiments, a structured surface is a substrate having an array of microwells. Each well has an interior surface defining an upper aperture and a nadir, wherein the upper aperture of each well has a diametric dimension in a range from 200 micrometers to 500 micrometers, or in a range from 100 micrometers to 2000 micrometers. The apparatus also includes a plurality of spacers to maintain a gap between stacked plates. The spacers can include plural spaced apart rails extending from the first major surface along a length of the first major surface. A plurality of flow channels are defined between adjacent rails.

In some embodiments, the wells can be configured such that cells cultured in the wells form spheroids. For example, interior surfaces of the well can be non-adherent to cells to cause the cells in the wells to associate with each other and form spheres. The spheroids can expand to size limits imposed by the geometry of the wells. In some embodiments, the wells can be coated with an ultra-low binding material to make the wells non-adherent to cells.

The formation of three-dimensional (3D) cell agglomerates such as spheroids, as opposed to two-dimensional cell culture in which the cells form a monolayer on a surface, can increase the density of cells grown in a cell culture apparatus. Increased cell density can lead to an increased metabolic burden. In various embodiments described herein diffusion of metabolic gasses occurs through the plate material, rather than relying on flow of cell culture medium, are described. Such apparatuses can be better suited to meet the metabolic demands of cells cultured in high density.

Cells cultured in three dimensions, such as spheroids, can exhibit more in vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. Cells cultured in three dimensions more closely resemble in vivo tissue in terms of cellular communication and the development of extracellular matrices. Spheroids thus provide a superior model for cell migration, differentiation, survival, and growth and therefore provide better systems for research, diagnostics, and drug efficacy, pharmacology, and toxicity testing.

In some embodiments, the devices are configured such that cells cultured in the devices form spheroids. For example, the wells in which cells are grown can be non-adherent to cells to cause the cells in the wells to associate with each other and form spheres. The spheroids expand to size limits imposed by the geometry of the wells. In some embodiments, the wells are coated with a non-adherent material. In embodiments, the non-adherent material is an ultra-low binding material to make the wells non-adherent to cells.

Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. In embodiments, these may be ultra low binding materials. The combination of, for example, non-adherent wells, well geometry (e.g., size and shape), and/or gravity induce cells cultured in the wells to self-assemble into spheroids. Some spheroids maintain differentiated cell function indicative of a more in vivo-like, response relative to cells grown in a monolayer. Other cells types, such as mesenchymal stromal cells, when cultured as spheroids retain their pluripotency, In some embodiments, the systems, devices, and methods herein comprise one or more cells. In some embodiments, the cells are cryopreserved. In some embodiments, the cells are in three dimensional culture. In some such embodiments, the systems, devices, and methods comprise one or more spheroids. In some embodiments, one or more of the cells are actively dividing. In some embodiments, the systems, devices, and methods comprise culture media (e.g., comprising nutrients (e.g., proteins, peptides, amino acids), energy (e.g., carbohydrates), essential metals and minerals (e.g., calcium, magnesium, iron, phosphates, sulphates), buffering agents (e.g., phosphates, acetates), indicators for pH change (e.g., phenol red, bromo-cresol purple), selective agents (e.g., chemicals, antimicrobial agents), etc.). In some embodiments, one or more test compounds (e.g., drug) are included in the systems, devices, and methods.

A wide variety of cell types may be cultured. In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown. Cells grown in spheroids may be natural cells or altered cells (e.g., cell comprising one or more non-natural genetic alterations). In some embodiments, the cell is a somatic cell. In some embodiments, the cell is a stem cell or progenitor cell (e.g., embryonic stem cell, induced pluripotent stem cell) in any desired state of differentiation (e.g., pluripotent, multi-potent, fate determined, immortalized, etc.). In some embodiments, the cell is a disease cell or disease model cell. For example, in some embodiments, the spheroid comprises one or more types of cancer cells or cells that can be induced into a hyper-proliferative state (e.g., transformed cells). Cells may be from or derived from any desired tissue or organ type, including but not limited to, adrenal, bladder, blood vessel, bone, bone marrow, brain, cartilage, cervical, corneal, endometrial, esophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid. In some embodiments, the cells are mammalian cells (e.g., human, mice, rat, rabbit, dog, cat, cow, pig, chicken, goat, horse, etc.).

The cultured cells find use in a wide variety of research, diagnostic, drug screening and testing, therapeutic, and industrial applications.

In some embodiments, the cells are used for production of proteins or viruses. Systems, devices, and methods that culture large numbers of spheroids in parallel are particularly effective for protein production. Three-dimensional culture allows for increased cell density, and higher protein yield per square centimeter of cell growth surface area. Any desired protein or viruses for vaccine production may be grown in the cells and isolated or purified for use as desired. In some embodiments, the protein is a native protein to the cells. In some embodiments, the protein is non-native. In some embodiments, the protein is expressed recombinantly. Preferably, the protein is overexpressed using a non-native promoter. The protein may be expressed as a fusion protein. In some embodiments, a purification or detection tag is expressed as a fusion partner to a protein of interest to facilitate its purification and/or detection. In some embodiments, fusions are expressed with a cleavable linker to allow separation of the fusion partners after purification.

In some embodiments, the protein is a therapeutic protein. Such proteins include, but are not limited to, proteins and peptides that replace a protein that is deficient or abnormal (e.g., insulin), augment an existing pathway (e.g., inhibitors or agonists), provide a novel function or activity, interfere with a molecule or organism, or deliver other compounds or proteins (e.g., radionuclides, cytotoxic drugs, effector proteins, etc.). In some embodiments, the protein is an immunoglobulin such as an antibody (e.g., monoclonal antibody) of any type (e.g., humanized, bi-specific, multi-specific, etc.). Therapeutic protein categories include, but are not limited to, antibody-based drugs, Fc fusion proteins, anticoagulants, antigens, blood factor, bone morphogenetic proteins, engineered protein scaffolds, enzymes, growth factors, hormones, interferons, interleukins, and thrombolytics. Therapeutic proteins may be used to prevent or treat cancers, immune disorders, metabolic disorders, inherited genetic disorders, infections, and other diseases and conditions.

In some embodiments, the protein is a diagnostic protein. Diagnostic proteins include, but are not limited to, antibodies, affinity binding partners (e.g., receptor-binding ligands), inhibitors, antagonists, and the like. In some embodiments, the diagnostic protein is expressed with or is a detectable moiety (e.g., fluorescent moiety, luminescent moiety (e.g., luciferase), colorimetric moiety, etc.).

In some embodiments, the protein is an industrial protein. Industrial proteins include, but are not limited to, food components, industrial enzymes, agricultural proteins, analytical enzymes, etc.

In some embodiments, the cells are used for drug discovery, characterization, efficacy testing, and toxicity testing. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug interaction assessment, dose assessment, adsorption assessment, disposition assessment, metabolism assessment, elimination studies, etc. Specific cells types may be employed for specific tests (e.g., hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity, skeletal myocytes for rhabdomyolysis, etc.). Treated cells may be assessed for any number of desired parameters including, but not limited to, membrane integrity, cellular metabolite content, mitochondrial functions, lysosomal functions, apoptosis, genetic alterations, gene expression differences, and the like.

In some embodiments, the cell culture devices are a component of a larger system. In some embodiments, the system comprises a plurality (e.g., 2, 3, 4, 5, . . . , 10, . . . , 20, . . . , 50, . . . , 100, . . . , 1000, etc.) of such cell culture devices. In some embodiments, the system comprises an incubator for maintaining the culture devices at optimal culture conditions (e.g., temperature, atmosphere, humidity, etc.). In some embodiments, the system comprises detectors for imaging or otherwise analyzing cells. Such detectors include, but are not limited to, fluorimeters, luminometers, cameras, microscopes, plate readers (e.g., PERKIN ELMER ENVISION plate reader; PERKIN ELMER VIEWLUX plate reader), cell analyzers (e.g., GE IN Cell Analyzer 2000 and 2200; THERMO/CELLOMICS CELLNSIGHT High Content Screening Platform), and confocal imaging systems (e.g., PERKIN ELMER OPERAPHENIX high throughput content screening system; GE INCELL 6000 Cell Imaging System). In some embodiments, the system comprises perfusion systems or other components for supplying, re-supplying, and circulating culture media or other components to cultured cells. In some embodiments, the system comprises robotic components (e.g., pipettes, arms, plate movers, etc.) for automating the handing, use, and/or analysis of culture devices.

Referring now to FIG. 1 a schematic side view of an embodiment of a plate 110, or portion thereof, having a first major surface 112 and an opposing second major surface 114 is shown. The first major surface 112 defines a structured surface for culturing cells. The structured surface of the first major surface 112 is a substrate having a plurality of wells 115. Spheroids 200 are shown residing inside wells 115.

A structured surface of a plate as described herein may define any suitable number of wells that may have any suitable size or shape. The wells define a volume based on their size and shape. In many embodiments, one or more or all of the wells are symmetric around a longitudinal axis. In some embodiments, the longitudinal axes of one or more or all of the wells are parallel with one another. The wells may be uniformly or non-uniformly spaced. In embodiments, the wells are uniformly spaced. One or more or all the wells can have the same size and shape or can have different sizes and shapes.

Figure 2:
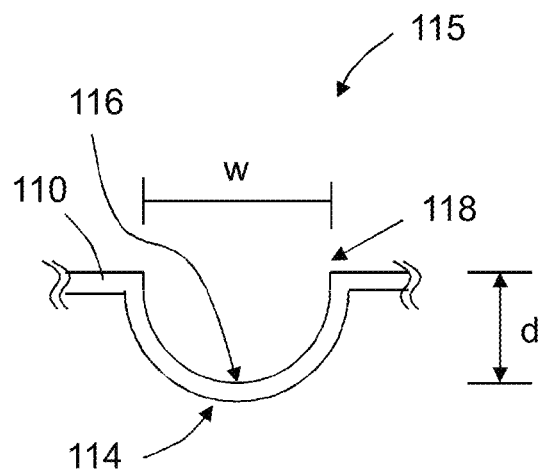
FIG. 2 is a schematic cross-sectional view of an embodiment of a well of a structured surface.
Figure 3:
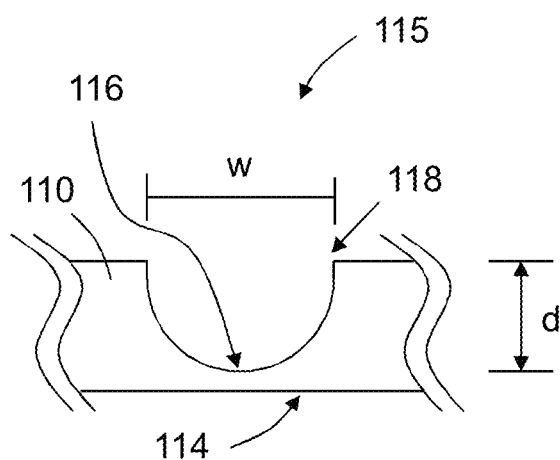
FIG. 3 is a schematic cross-sectional view of an embodiment of a well of a structured surface.

Referring now to FIG. 2 and FIG. 3, schematic cross-sectional views of some embodiments of wells 115 are depicted. As described above with regard to FIG. 1, the wells 115 are defined by the structured surface of plate 110. The second major surface 114 or non-culture surface of plate 110 can have any suitable shape. As depicted in FIG. 2, the plate 110 forming the well 115 has a thickness along the well that is substantially constant and is relatively thin. In contrast, the thickness of the plate 110 defining the well 115 in FIG. 3 varies along the well, such that proximate to upper aperture 118 of the well, the thickness is relatively large, and at nadir 116 the thickness is relatively thin.

In some embodiments, the wells 115 are gas permeable through the plate 110, i.e., through the well wall. The gas permeability of the wells 115 through the plate 110 to second major surface 114 will depend in part on the material of the plate and the thickness of the plate along the well. All else being equal, the well in FIG. 2 would be more gas permeable than the well in FIG. 3. However, depending on the material used and the thickness employed, plate 110 shaped in either FIG. 2 or FIG. 3 may be sufficiently gas permeable for purposes of the present disclosure.

In embodiments, the wells 115 have an oxygen transmission rate through the plate 110 of 2000 cc/m$^2$/day or greater. In embodiments, the wells have a gas permeability through the plate of 3000 cc/m$^2$/day or greater. In embodiments, the wells have a gas permeability through the plate of 5000 cc/m$^2$/day or greater.

Plate 110 may be formed of any material having a suitable gas permeability over at least a portion of the well. Examples of suitable materials include polydimethylsiloxane (PDMS), (poly)4-methylpentene (PMP), polyethylene (PE), and polystyrene (PS). PDMS can have a high degree of gas permeability and can be achieve sufficient gas permeabilities at thicknesses up to three to four centimeters. PMP can achieve sufficient gas permeabilities at thicknesses up to about 0.03 inches. In some embodiments, PMP having a thickness in a range of about 0.001 inch to about 0.025 inches is used to form wells. PE or PS can achieve sufficient gas permeabilities at thicknesses up to 0.005 inches, such as 0.003 inches or less. Some thinner plates may not have sufficient structural integrity. To compensate for poor structural integrity, an open frame, standoffs, or the like can be used to support the plate, or a structured surface portion thereof, from the bottom.

In embodiments, where the wells 115 are not gas permeable through the plate 110, thicker or non-gas permeable materials can be used. Examples of suitable materials for forming plates or other cell culture components described herein include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

Still with reference to FIGS. 2 and 3, the wells 115 have a depth d defined by the height from nadir 116 to upper aperture 118. The wells 115 also have a diametric dimension w, such as a diameter, width, etc., across the well defined by the upper aperture 118. The wells may have any suitable depth d and diametric dimension w. In some embodiments, the depth d, diametric dimension w and shape of the well, along with the material forming the well, serve to define a volume in which cells can grow.

In some embodiments, the inner surface of the wells 115 is non-adherent to cells. The wells may be formed from non-adherent material or may be coated with non-adherent material to form a non-adherent well. Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. The combination of, for example, non-adherent wells, well geometry, and gravity can induce cells cultured in the wells to self-assemble into spheroids. Some spheroids can maintain differentiated cell function indicative of a more in vivo like response relative to cells grown in a monolayer.

The combination of, for example, non-adherent wells, well geometry, and gravity can define a confinement volume in which growth of cells cultured in the wells is limited.

In some embodiments, one or more wells have a concave surface, such as a hemi-spherical surface, a conical surface having a rounded bottom, and the like surface geometries or a combination thereof. The well and well bottom can ultimately terminate, end, or bottom-out in a spheroid conducive rounded or curved surface, such as a dimple, a pit, and like concave frusto-conical relief surfaces, or combinations thereof. Other shapes and construction of gas-permeable spheroid-conducive wells are described in commonly-assigned U.S. patent application Ser. No. 14/087,906, which application is hereby incorporated herein by reference in its entirety to the extent that it does not conflict with the present disclosure.

In some embodiments, well bottoms are flat or come to a point. Well bottoms may have any other suitable shape or dimension.

In some embodiments, the wells 115 described herein have a diametric dimension w in a range from about 200 micrometers to about 500 micrometers, e.g., 200, 250, 300, 350, 400, 450 or 500 micrometers, including ranges between any of the foregoing. Such diametric dimensions can control the size of a spheroid grown therein such that cells at the interior of the spheroid are maintained in a healthy state. In some embodiments, the wells 115 have a depth d in a range from about 200 micrometers to about 500 micrometers, e.g., 200, 250, 300, 350, 400, 450 or 500 micrometers, including ranges between any of the foregoing. Of course, other suitable dimensions may also be employed.

Figure 4:
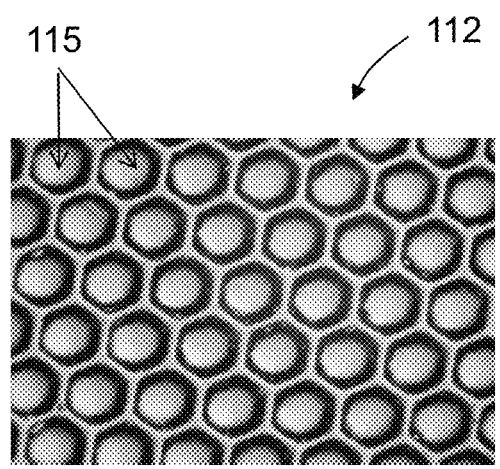
FIG. 4 is an image of an embodiment of a substrate having a structured surface.
Figure 5:
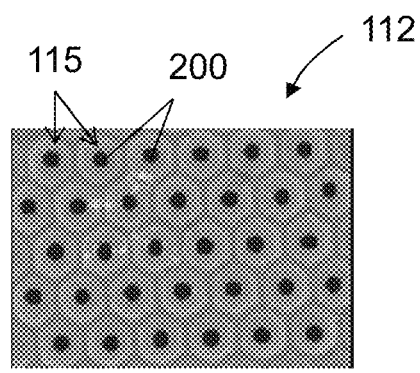
FIG. 5 is a schematic top view of cells grown in wells of an embodiment of a structured surface.

In some embodiments, the structured surface defining the wells includes an array of hexagonal close-packed well structures. An image of an embodiment of a first major surface 112 having such a structured surface is shown in FIG. 4, showing the surface 112 forming wells 115. FIG. 5 is a schematic drawing showing cells 200 grown in wells 115 of an embodiment of a plate having a first major surface 112 including a structured surface defining a hexagonal close-packed well structure. In some embodiments, the cells 200 within each well 115 form a single spheroid.

A structured surface as described herein can be formed in any suitable matter. For example, a plate or film can be molded or embossed to form the structured surface. In a further example, a heated reform tool may be applied to a molded plate. Or, a structured surface may be formed by injection molding.

A plate having a structured surface as described above may be incorporated into a cell culture apparatus. The plates may be stacked to form a cell culture apparatus. In embodiments, the stacked plates are separated by rails, with flow channels formed above a structured surface between adjacent rails.

Figure 6A:
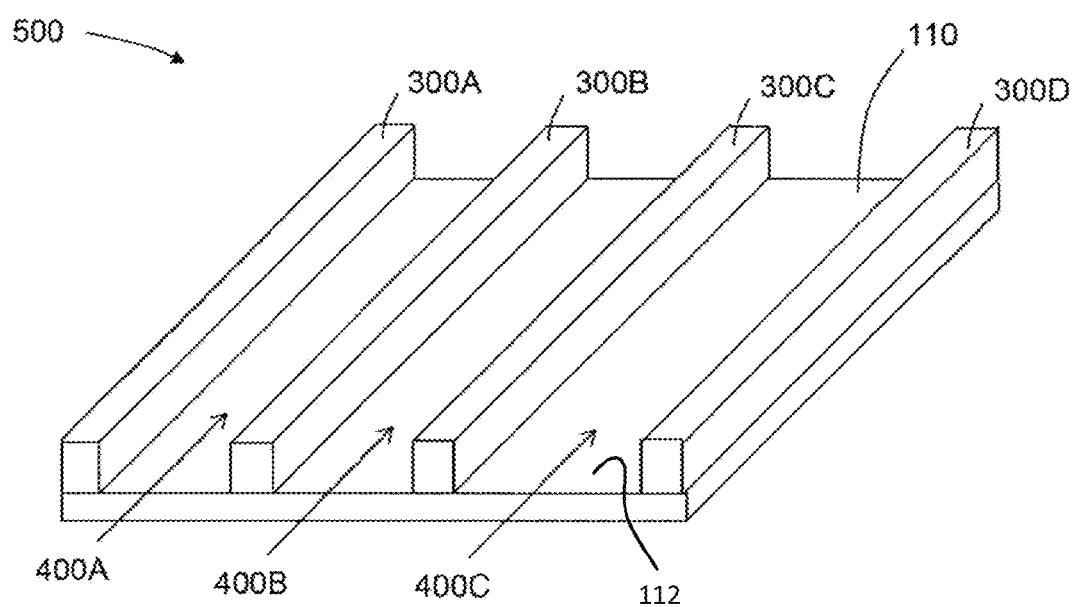
FIGS. 6A-C are schematic perspective views of an embodiments of plates and rails.
Figure 6B:
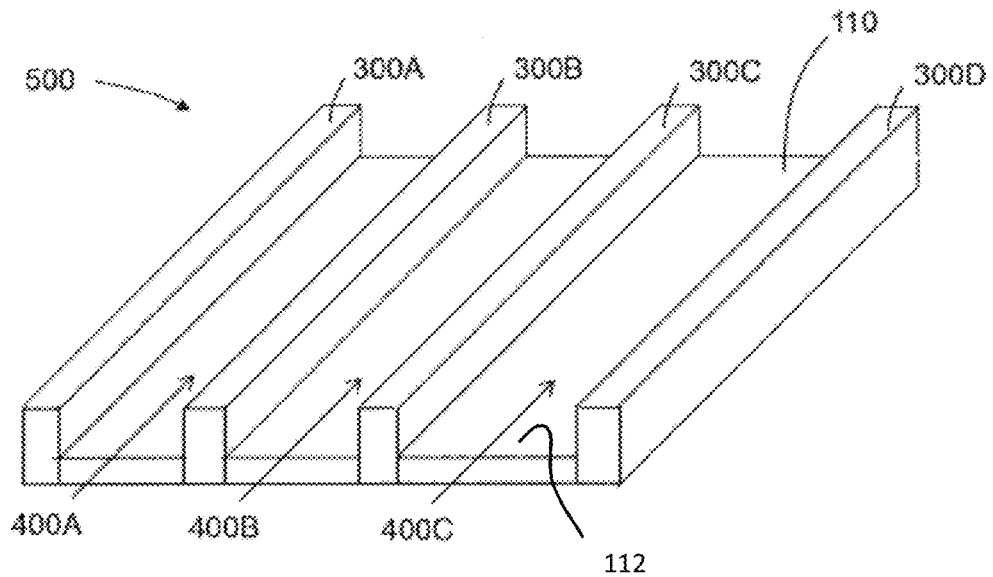
Figure 6C:
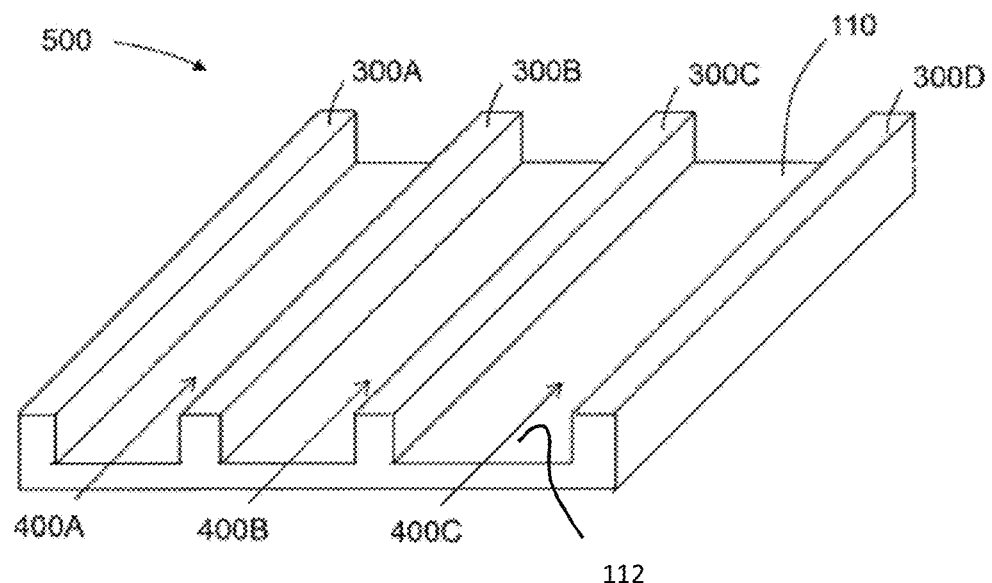

Referring now to FIGS. 6A-C, schematic perspective views of embodiments of a single stackable unit 500 having rails 300A, 300B, 300C, 300D and plates 110 are shown. The rails 300A, 300B, 300C, 300D extend from the plate 110 along the length of the plate. Flow channels 400A, 400B, 400C are formed between adjacent rails. In the embodiment depicted in FIG. 6A, rails 300A, 300B, 300C, 300D are disposed on the first major surface of the plate 110. In the embodiment depicted in FIG. 6B, the rails 300A, 300B, 300C, 300D extend below the first major surface of the plate. In the embodiment depicted in FIG. 6C, the plate 110 and rails 300A, 300B, 300C, 300D comprise a unitary part. The rails and plates can be assembled in any suitable manner. For example, the plate and rails can be molded as a single part. In embodiments, the plate or a portion thereof is over-molded to form the rails. In embodiments, the plate and rails are welded (e.g., thermal, laser, long IR or ultrasonic welding, or the like), adhered, solvent-bonded or the like. The plates and rails can form a unit 500, which can be stacked during assembly of a cell culture apparatus as described herein.

Figure 7:
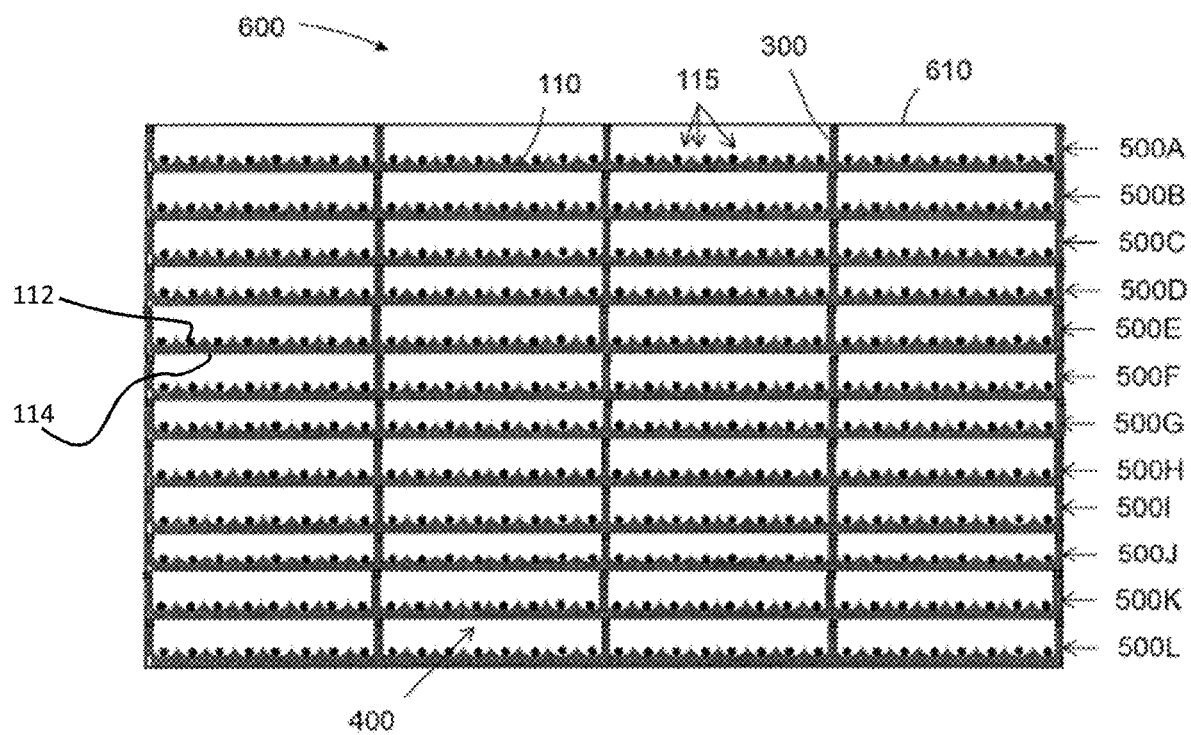
FIG. 7 is a schematic cross-sectional view of an embodiment of a cell culture apparatus.

Referring now to FIG. 7, a schematic cross-section of an embodiment of a cell culture apparatus 600 having a plurality of stacked units 500A-L is shown. Each unit includes a plate 110 and a plurality of rails 300. Flow channels 400 are formed between adjacent rails 300 above a first major surface 112 of the plate 110 and below an opposing second major surface 114 of an adjacent plate 110 of the above-stacked unit. A top plate 610 can be disposed above the top-most unit 500A. Each unit as a plurality of wells 115.

Figure 8:
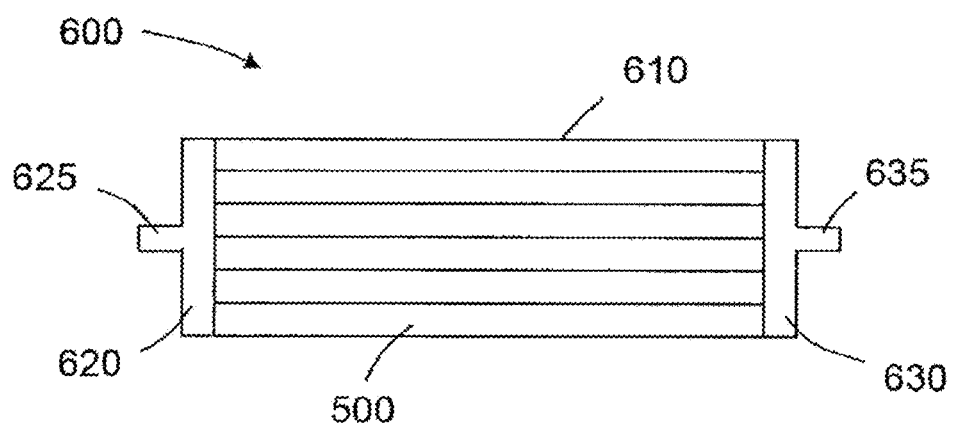
FIG. 8 is a schematic side view of an embodiment of a cell culture apparatus.

Referring now to FIG. 8, a schematic side view of an embodiment of cell culture apparatus 600 having an inlet manifold 620 defining an inlet port 625 and an outlet manifold 630 defining an outlet port 635 is shown. The apparatus 600 includes a plurality of stacked units 500 (e.g., units having a plate and rails as depicted in FIGS. 6A-C and FIG. 7). Each flow channel of each unit is in fluid communication with inlet port 625 via manifold 620 and is in fluid communication with outlet port 635 via manifold 630. In some embodiments, an expander having inlet port 625 can be used rather than a manifold. In some embodiments, a reducer having outlet port 635 can be used rather than a manifold. The top face of the apparatus is also shown 610.

Figure 9A:
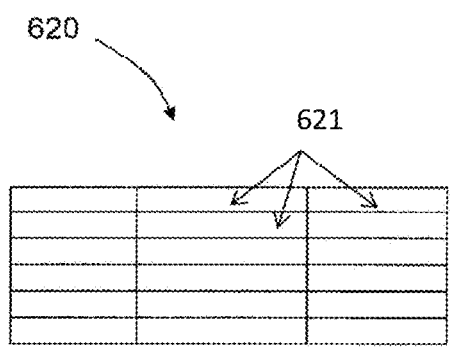
FIGS. 9A-B are schematic views of a face of an embodiment of a manifold (9A) and an expander (9B).
Figure 9B:
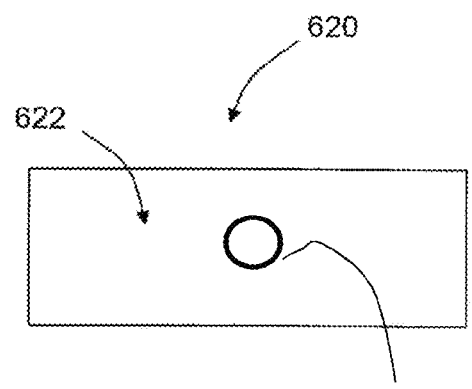

For example and with reference to FIGS. 9A-B, schematic views of the inside face of an embodiment of a manifold 620 (FIG. 9A) and the top face 622 of an embodiment of a manifold 620 (FIG. 9B) are shown. The manifold 620 in FIG. 9A defines a plurality of apertures 621, each of which can be aligned with, and welded to a respective flow channel to create a liquid tight seal. FIG. 9B shows the top face of the manifold with the port 625. Alternatively, because a face of the assembled units can essentially form a manifold with access to each flow channel a simplified expander 620 can be used to deliver cell culture fluid to the flow channels via the inlet port.

The inlet port and the outlet port can be coupled to tubing, which can be coupled to a pump for delivery of cell culture media to the flow channels of the cell culture apparatus.

Final assembly of a cell culture apparatus described herein can be performed in any suitable manner. For example, units can be welded, bonded, adhered or otherwise joined together. Manifolds, reducers or expanders can be welded, bonded, adhered or otherwise joined to assembled units. By way of example, the units can be inserted into a sleeve onto which inlet and outlet manifolds are joined; stacked and manifolded units could be assembled and over-molded; bags can be heat-shrunk to form a tight fit around the stacked units; units are stacked and packed into a formed chamber or formed bag; and the like.

Figure 10A:
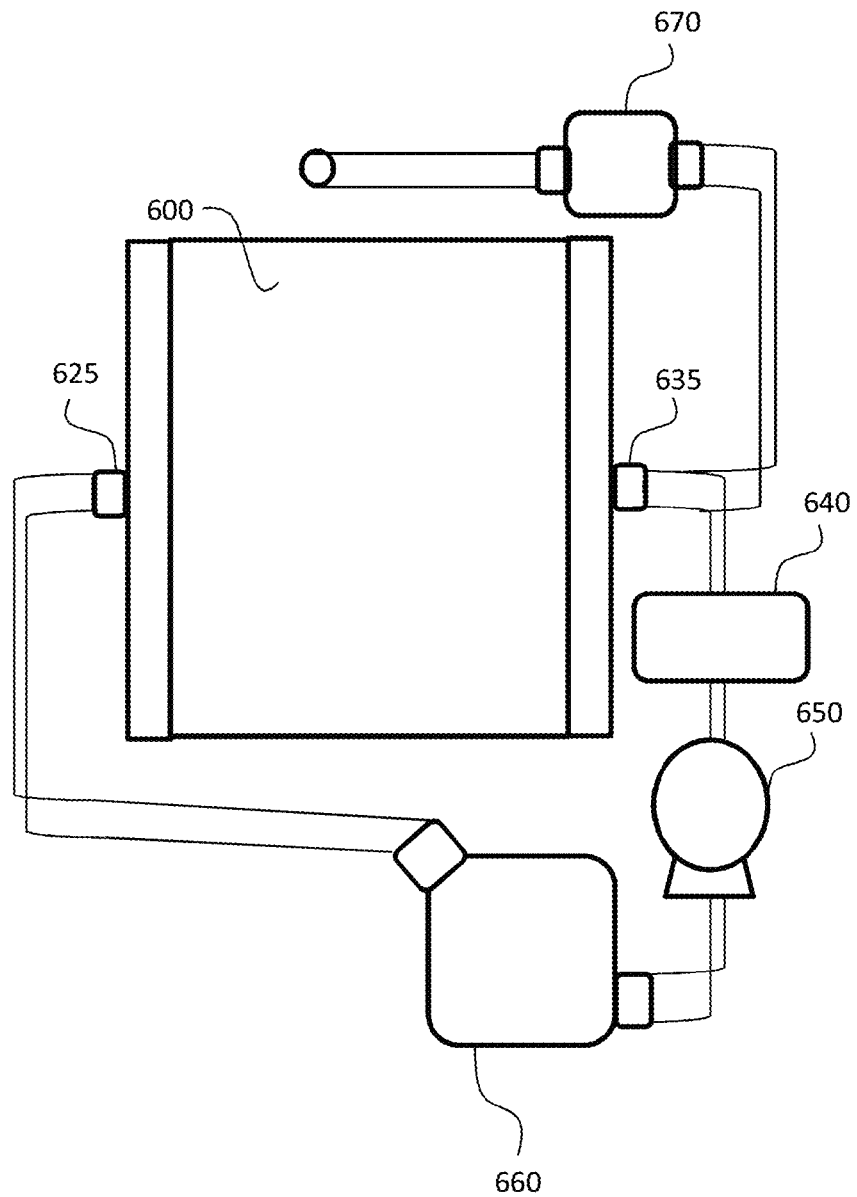
FIGS. 10A-B is a schematic diagram of an embodiment of a system operating in batch mode (10A) and continuous mode (10B).
Figure 10B:
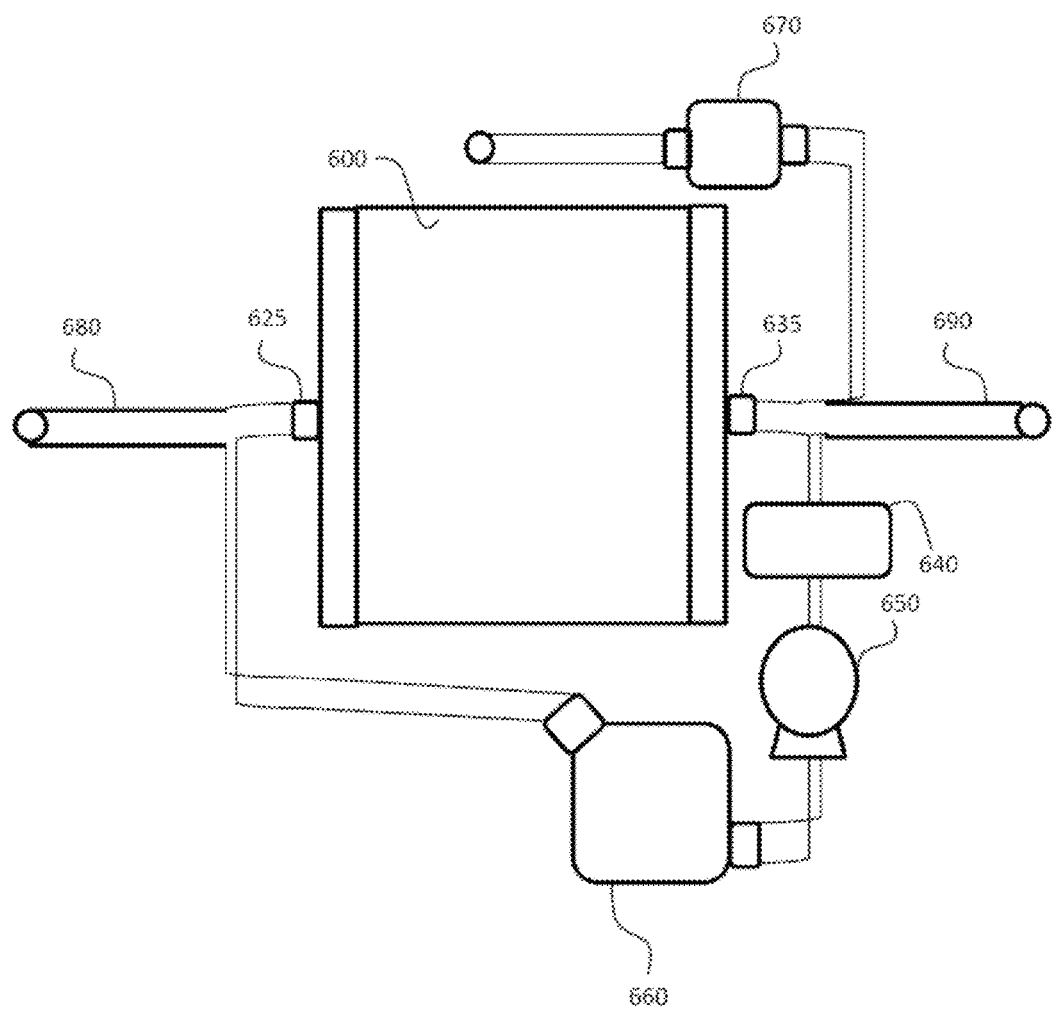

Referring now to FIGS. 10A-B, schematic diagrams of embodiments of systems employing embodiments of cell culture apparatuses 600 as described herein are shown. The diagram depicted in FIG. 10A illustrates the system in batch mode. Flow of media enters the culture apparatus 600 through input 625. The media is oxygenated by an optional oxygenator 660. The force of the flow is generated and controlled by recirculation pump 650, operably coupled to source of cell culture media. Media flows out of the culture apparatus 600 through output 635. The flow (e.g., flow rate) is managed by a controller 640 (e.g., via control of valves). The controller may also control gas flow to the oxygenator and control flow of supplemental nutrients or pH modifiers as desired or required. Cultured cells are harvested by directing media from the output 635 to a cell collection cartridge 670. Each of the components is connected by tubing, channels (e.g., microchannels) or any other desired fluid connectivity. The diagram in FIG. 10B illustrates the system in continuous mode. The system further includes an input flow channel 680 through which fluid flows into the cell culture apparatus 600 and an output flow channel 690 through which fluid can flow out of the cell culture apparatus 600. In some embodiments described below in which the cell culture apparatus is configured to allow diffusion of metabolic gases, an oxygenator can be omitted.

In embodiments where the inner surfaces of the wells of the structured surface of the plates are non-adherent to cells, the flow rate of cell culture media through the flow channels of the apparatus 600 can be increased to dislodge the cultured cells, which can be spheroids, from the wells to be carried with the flow of cell culture medium to cell collection cartridge. Lower flow rates can be used to grow and maintain cells within the wells. It will be understood that the shape and dimensions of the wells can be modified to alter flow rates for maintaining the cells in the wells or to dislodge the cells from the wells.

Figure 11A:
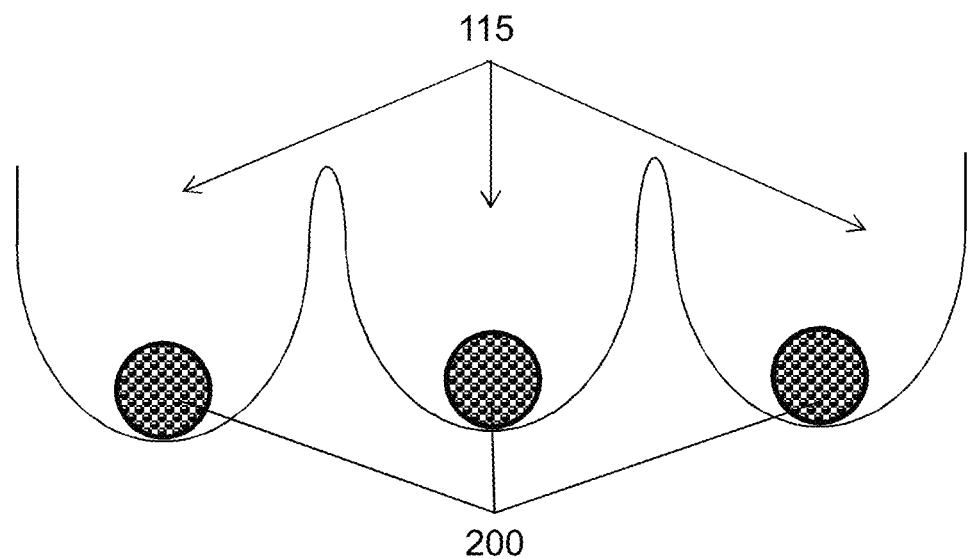
FIGS. 11A-B are schematic sectional views of an embodiments of wells.
Figure 11B:
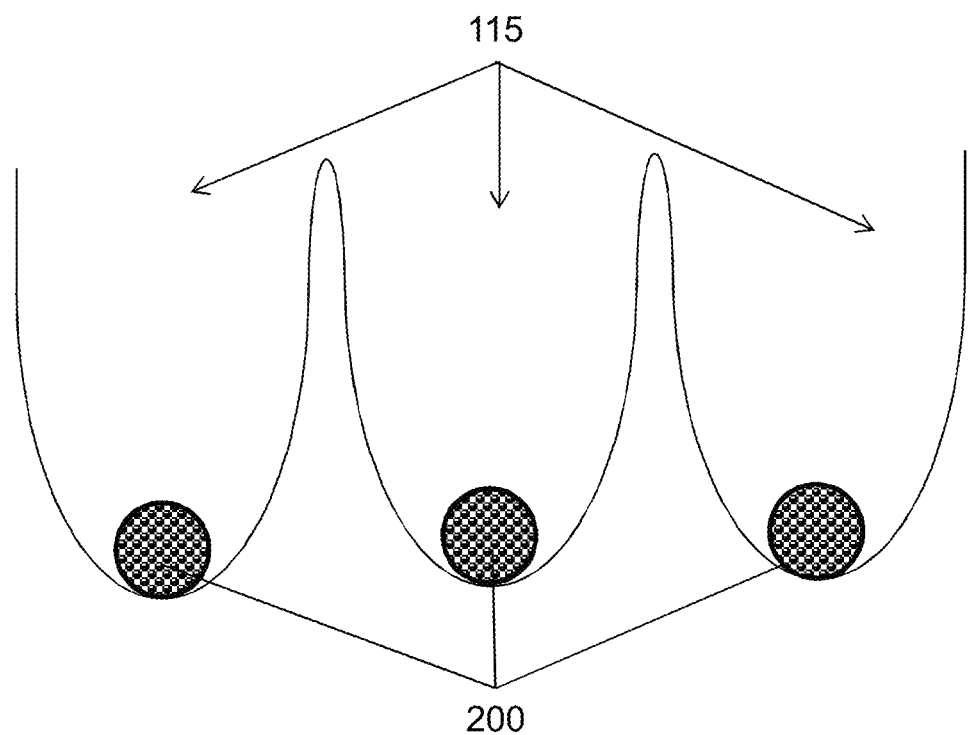

By way of example and with reference to FIGS. 11A-11B, schematic sectional views of alternative well geometries are shown. The wells 115 in FIG. 11B are deeper than the wells 115 in FIG. 11A and thus the spheroids 200 are deeper in the wells 115 in FIG. 11B than the wells 115 in FIG. 11A. Accordingly, the wells 115 in FIG. 11B allow for higher flow rates through the cell culture apparatus without dislodging the spheroids 200. Similarly, the wells 115 in FIG. 11A allow for dislodgment of the spheroids 200 at lower flow rates to facilitate harvesting. As discussed above, wells of structured surfaces of plates described herein can have any suitable geometry. The shape and size and characteristics of the well can be tuned for purposes of tuning cell properties (e.g., spheroid formation), for purposes of facilitating cell dislodgement, for purposes of ensuring sufficient nutrient and gas distribution to cultured cells, and the like, depending on the needs of the user.

In some embodiments, gas flow channels can be formed in the rails that coextend with the plates. In such embodiments the rails may be formed from gas permeable materials having sufficient thicknesses to allow metabolic gas exchange from a flow channel adjacent to the rail. Examples of suitable gas permeable materials and thicknesses are described above. In some embodiments, the rails are formed from PDMS, which is relatively gas permeable. By way of example, the rails can be formed from extruded PDMS that has air channel running therethrough. PDMS can be either thermoset or thermoplastic PDMS, such as Geniomer 145 from Wacker which can have higher gas exchange rates than thermoset PDMS. PDMS, however, is well known to bind small molecules, which can be undesirable for cell culture. This could be avoided with multilayer extrusion, overmolding, coatings or other treatments to create barriers to absorption which can also act as a non-cell adhesive layer. The air channels within the rails can run the length or height of the rails. Multiple air channels can be formed in the rails For example and with reference to FIG. 12, a schematic sectional view of stacked units 500A, 500B, 500C, 500D, each having a plate 110 and rails 300 with flow channels 400 formed between rails (e.g., as described above) is depicted. Spheroids 200 are shown with wells 115 of the structured surface of plate 110. In the depicted embodiment, rails 300 define air channels 310 that run the length of the rail. The thickness of the rail 300 between the channel 310 and an adjacent media flow channel 400 is sufficiently small to allow exchange of metabolic gases through the material of the rail.

Figure 13:
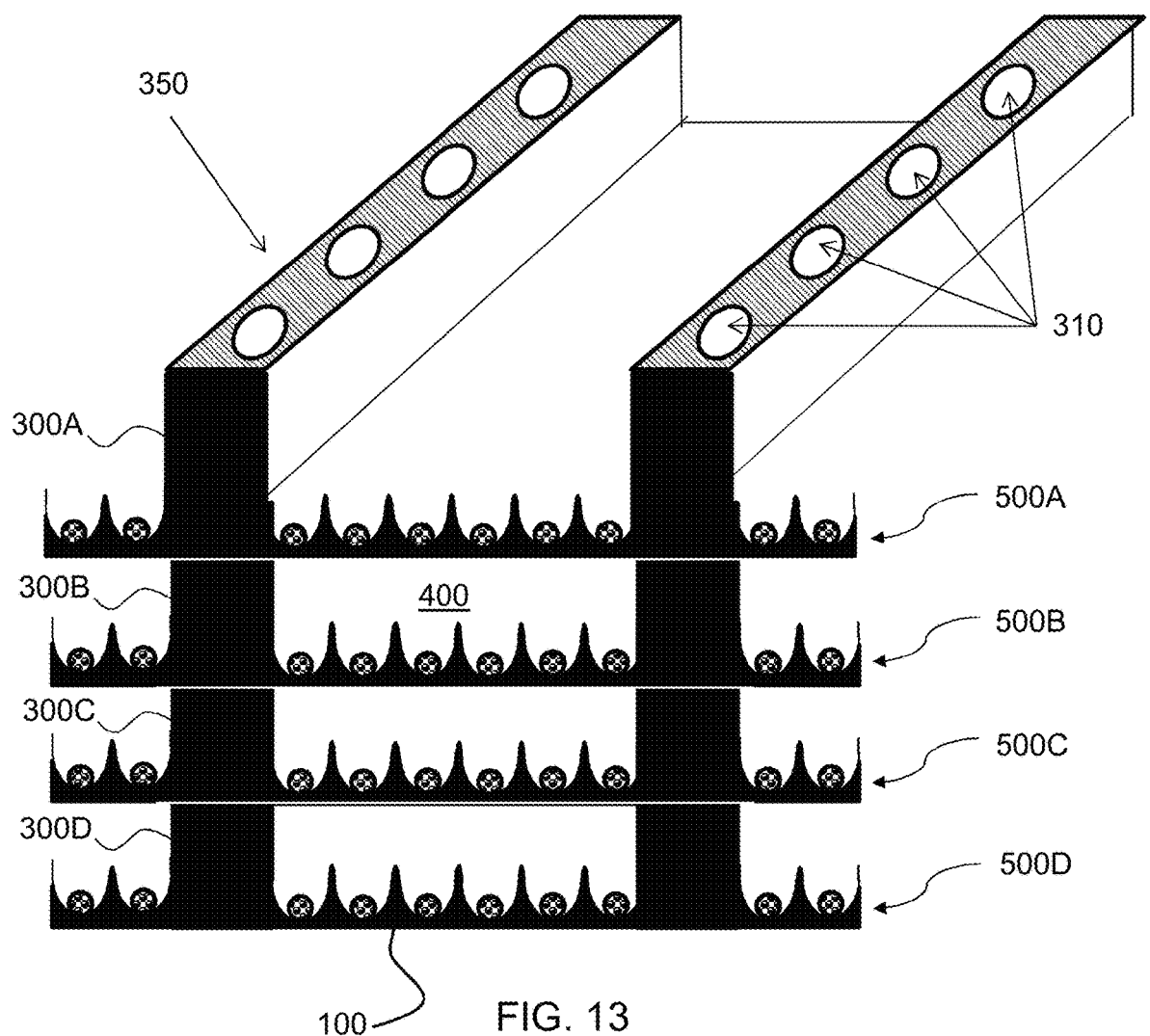
FIG. 13 is a schematic cut-away perspective view of embodiments of stacked units of plates and rails.

Referring now to FIG. 13, a schematic cut-away perspective view of stacked units 500A, 500B, 500C, 500D, each having a plate 110 and rails (e.g., rails 300A-D) with flow channels 400 formed between rails (e.g., as described above) is depicted. In this embodiment, each rail (e.g., rails 300A-D) forms a plurality of air channels 310 that extend the height of the rail. The air channels 310 of respective rails (e.g., rails 300A-D) are oriented such that when the units 500A, 500B, 500C, 500D are stacked, the air channels 310 align. When the units 500A, 500B, 500C, 500D are stacked, the rails form a wall 350 from the bottom-most unit (e.g., unit 500D) to the top-most unit (e.g., unit 500A). Columns of aligned air channels 310 formed by the rails (e.g., rails 300A-D) extend throughout the height of the assembled apparatus.

Figure 12:
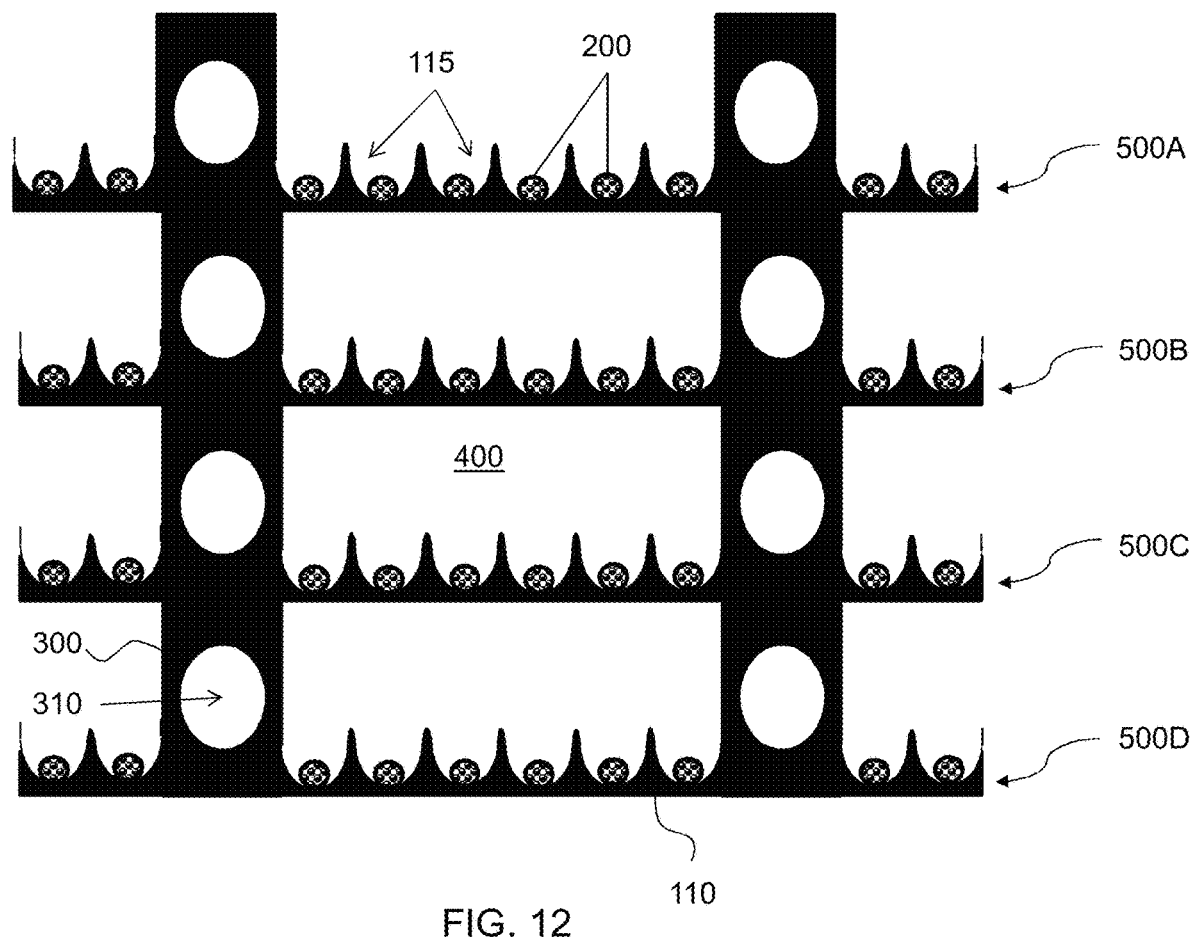
FIG. 12 is a schematic sectional view of embodiments of stacked units of plates and rails.

Regardless of the orientation of the air channels (e.g., along the length of the rails as depicted in FIG. 12 or along the height of the rails or wall as depicted in FIG. 13), the air channels can be connected to a manifold, expander or reducer to form single supply and vent port exiting the apparatus. In some embodiments, separate manifolds, expanders or reducers are coupled to both ends of the air channels of the apparatus to allow gas flow to be controlled through the stacked unit.

Figure 14:
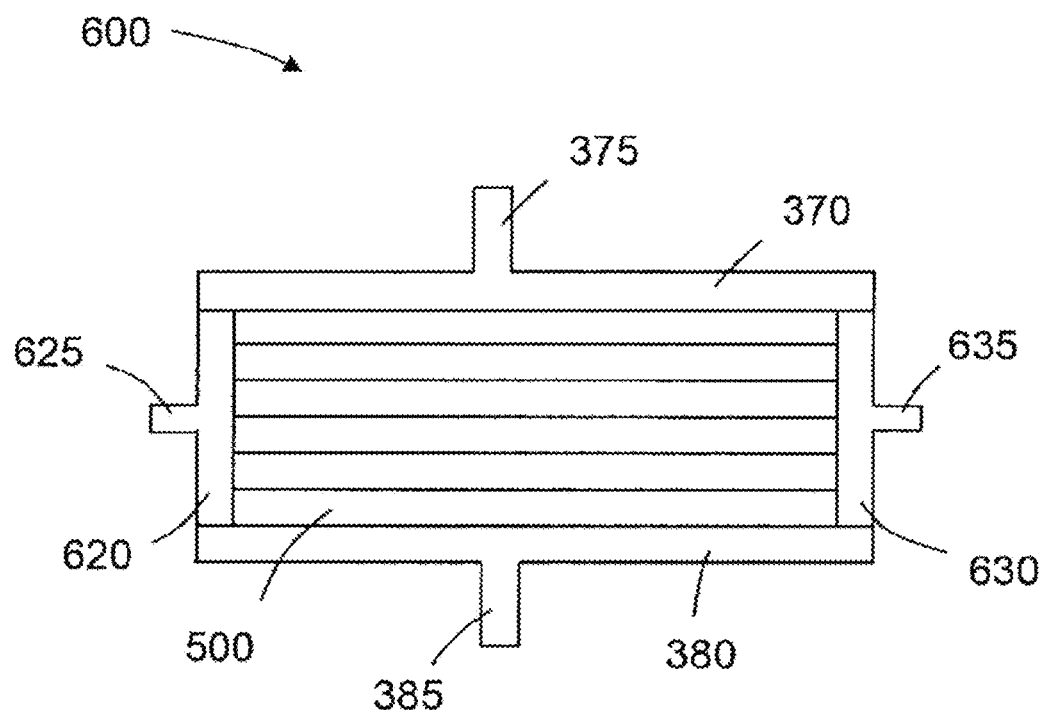
FIG. 14 is a schematic side view of an embodiment of a cell culture apparatus.

For example and with reference to FIG. 14, a schematic side view of an embodiment of a cell culture apparatus 600 including first 370 and second 380 vent manifolds is depicted. Many of the components depicted in the apparatus of FIG. 14 are depicted in, and described above with regard to the apparatus of FIG. 8. The apparatus 600 depicted in FIG. 14 can be envisioned with an assembly of units as depicted in FIG. 13 where the rails form walls that form air channel columns spanning the height of the apparatus. Vent manifolds 370 and 380 respectively form ports 375 and 385. Ports can be vented to atmosphere or can be coupled to tubing to provide a controlled gaseous environment to the apparatus.

Figure 15A:
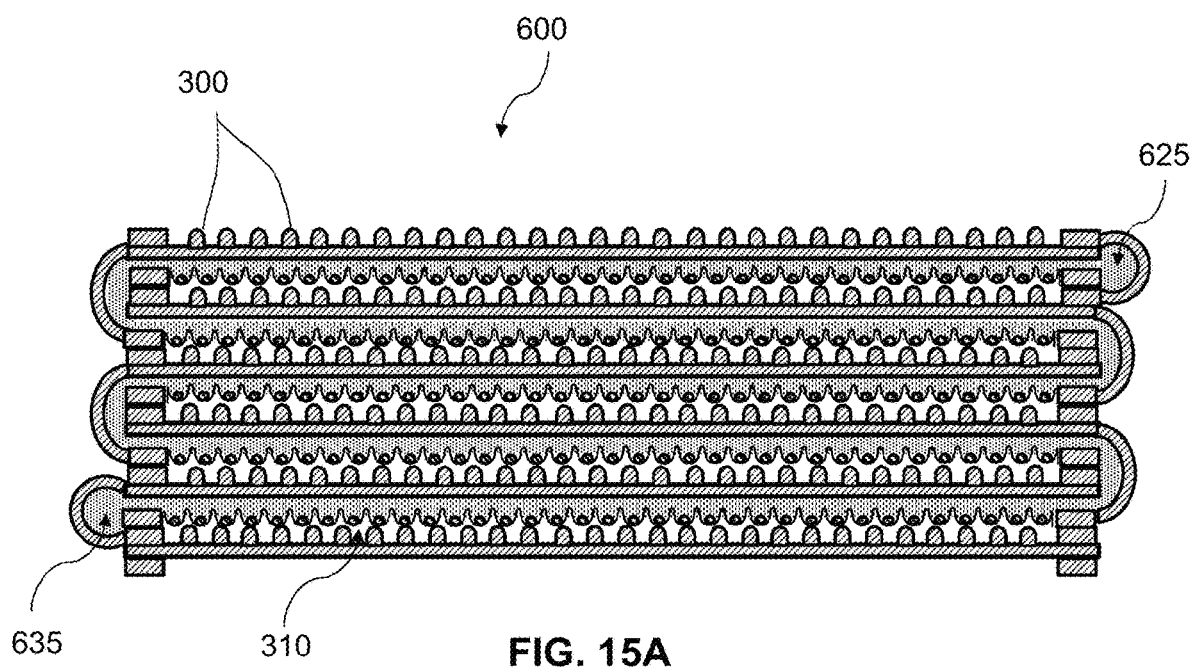
FIG. 15A shows a schematic cut-away perspective view of a cell culture apparatus 600, where the wells are formed from gas permeable material. In this exemplary embodiment, media enters one end of the apparatus through inlet port 625, and circulates through the whole apparatus before exiting (through outlet port 635), reversing flow through each chamber.
Figure 15B:
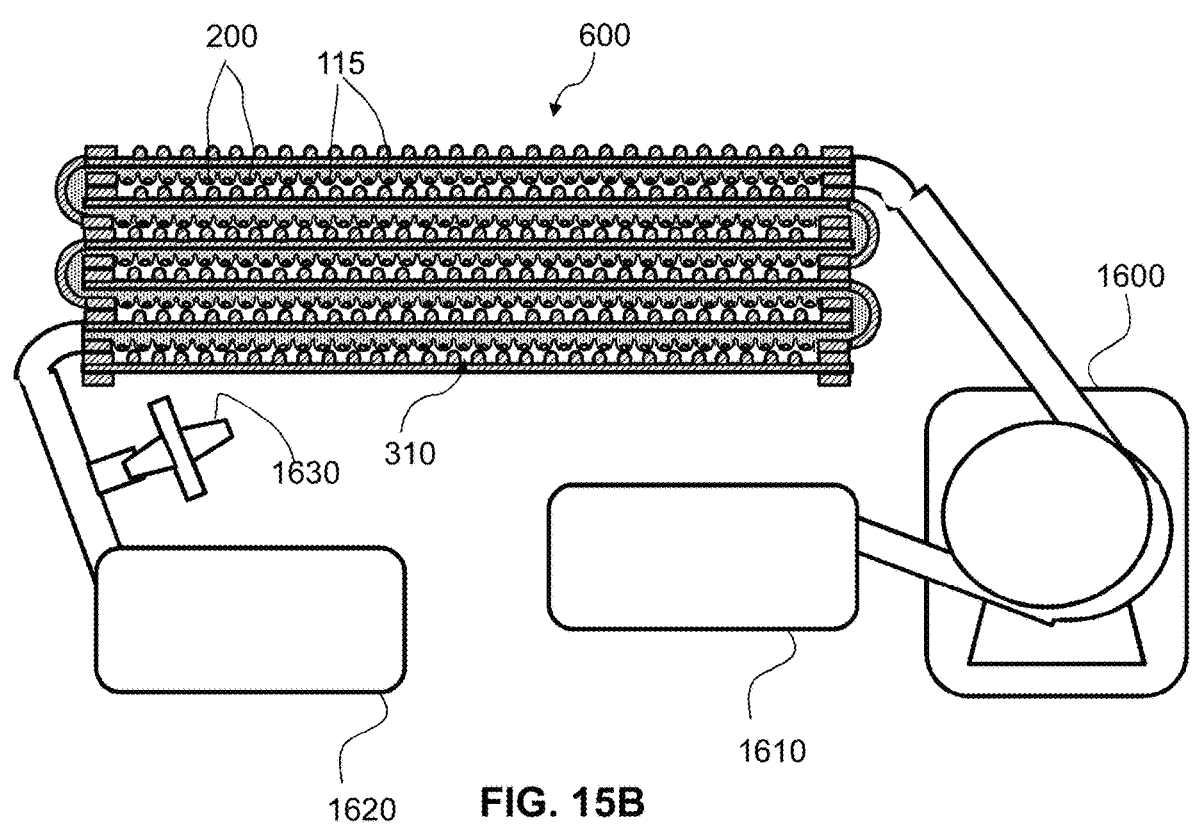
FIG. 15B shows a system for controlling flow through the cell culture apparatus illustrated in FIG. 15A.

Referring now to FIG. 15A, which shows a schematic cut-away perspective view of a cell culture apparatus 600, where the wells are formed from gas permeable material. In this exemplary embodiment, media enters one end of the apparatus through inlet port 625, and circulates through the whole apparatus, feeding spheroids 200 residing in microwells 115, before exiting (through outlet port 635), reversing flow through each chamber. The chambers/vessels may also have support bosses or posts (not shown) to maintain the appropriate structure. Air channels 310 run along the bottom of the gas permeable wells, allowing air exchange to feed the spheroids in the wells. Rails 300 allow formation of various air channels 310. FIG. 15B shows the cell culture apparatus of FIG. 15A, and specifically shows how air may infiltrate into the device via air channels 310 (white lines on front of apparatus). In this regard, as shown in FIG. 15B, no oxygenator is required since the air channels 310 (also called tracheal spaces) provide gas exchange through gas permeable well material. FIG. 15B further shows system component to manage media. A controller pump 1600 pumps fresh media from a fresh medium source 1610 to the cell culture apparatus 600. A waste containing 1620 collects used media. A valve 1630 may also be used to collect media and harvest compounds that might exist in the media, as the media is exiting the apparatus.

Figure 16A:
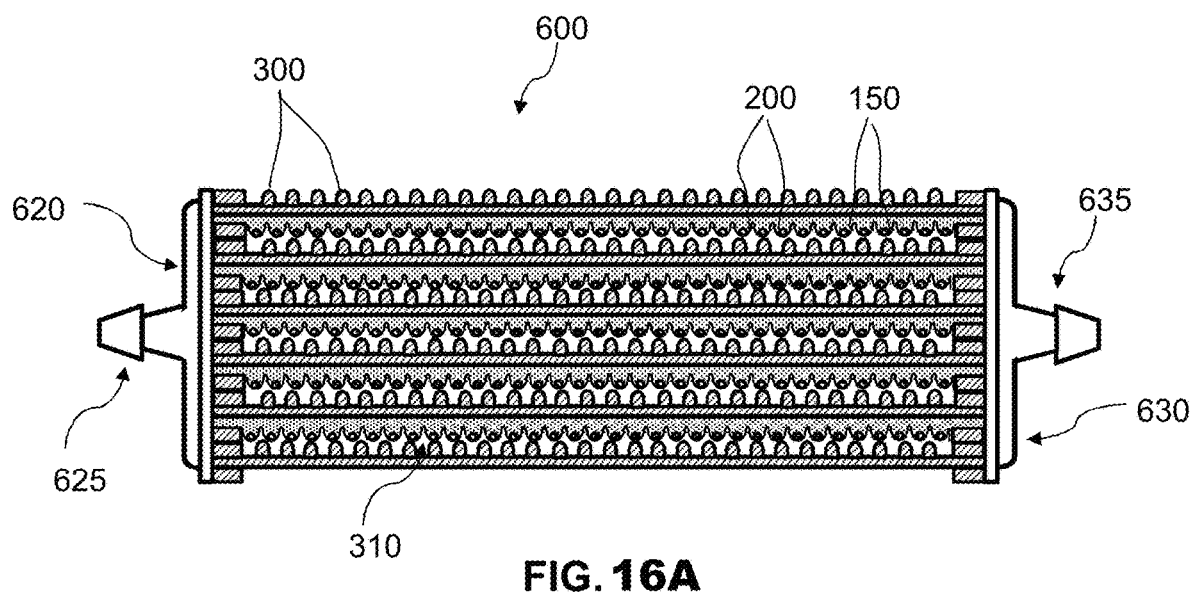
FIG. 16A shows a schematic cut-away perspective view of a cell culture apparatus 600, where the wells are formed from gas permeable material. In this exemplary embodiment, media enters through the inlet port 625 and distributes (via inlet manifold 620) to all compartments before exiting the opposite end through outlet manifold 630 attached to the outlet port 635.
Figure 16B:
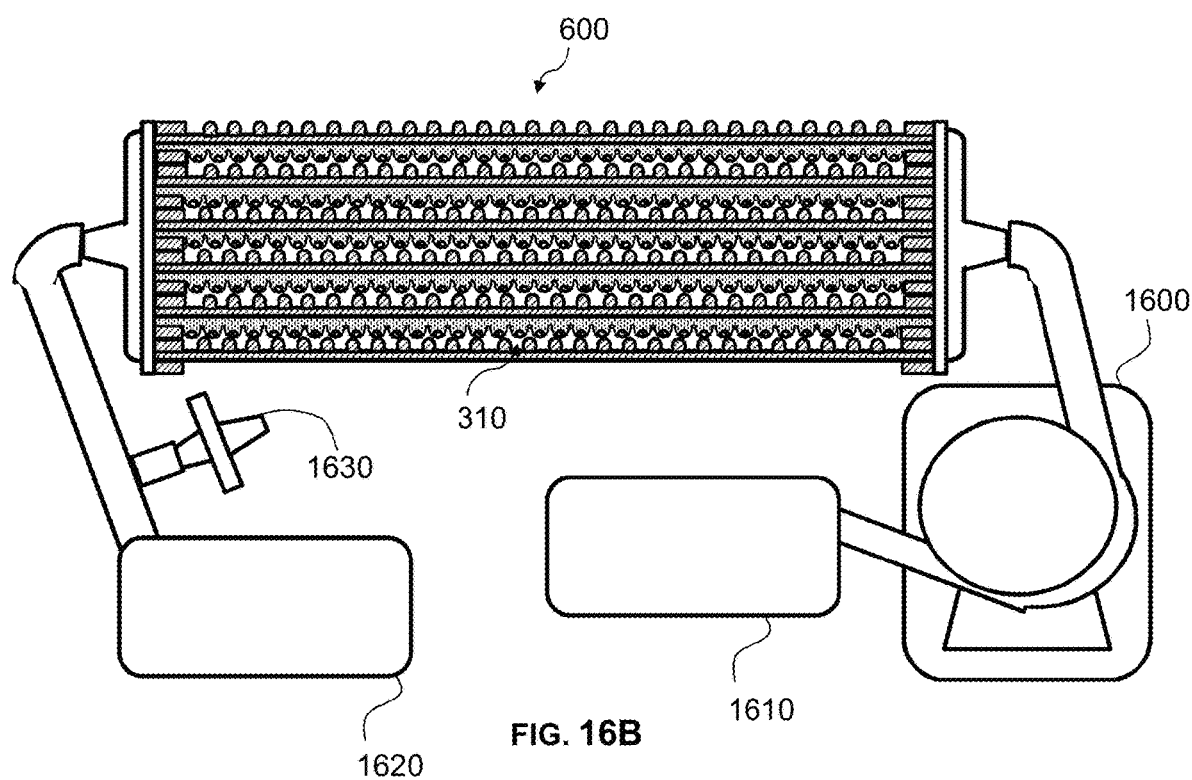
FIG. 16B shows a system for controlling flow through the cell culture apparatus illustrated in FIG. 16A.

Referring now to FIG. 16A, which shows a schematic cut-away perspective view of a cell culture apparatus 600, where the wells are formed from gas permeable material. In this exemplary embodiment, media enters through the inlet port 625 and distributes (via inlet manifold 620) to all compartments before exiting the opposite end through outlet manifold 630 attached to the outlet port 635. The chambers/vessels may also have support bosses or posts (not shown) to maintain the appropriate structure. Air channels 310 run along the bottom of the gas permeable wells, allowing air exchange to feed the spheroids in the wells. Rails 300 allow formation of various air channels 310. FIG. 16B shows the cell culture apparatus of FIG. 16A, and specifically shows how air may infiltrate into the device via air channels 310 (white lines on front of apparatus). In this regard, as shown in FIG. 16B, no oxygenator is required since the air channels 310 (also called tracheal spaces) provide gas exchange through gas permeable well material. FIG. 16B further shows system component to manage media. A controller pump 1600 pumps fresh media from a fresh medium source 1610 to the cell culture apparatus 600. A waste containing 1620 collects used media.

Figures 17A, 17B:
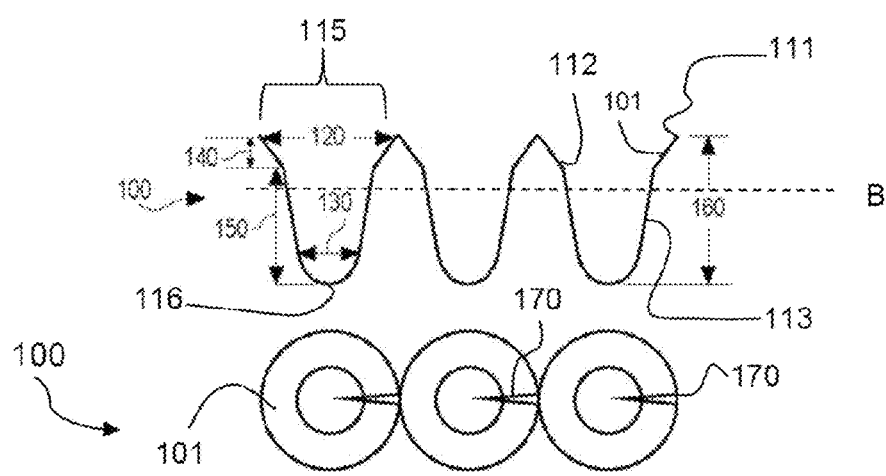
FIGS. 17A and B are schematic drawings of an exemplary embodiment of an array of wells 100.
FIG. 17B is a top-down drawing of the exemplary embodiment of an array of wells, taken at line B-B of FIG. 17A.
Figures 18A, 18B:
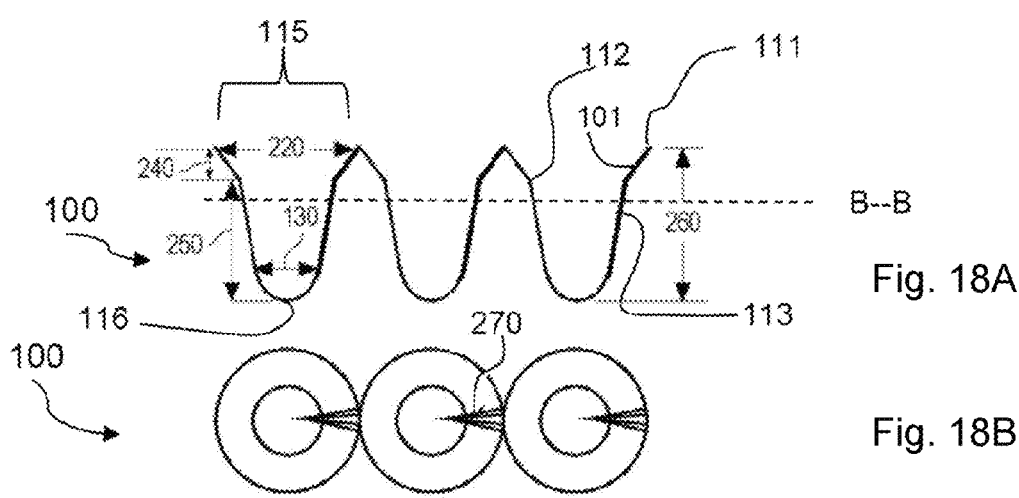
FIGS. 18A and B are schematic drawings of another exemplary embodiment of an array of wells 100.
FIG. 18B is a top-down drawing of the exemplary embodiment of an array of wells, taken at line B-B of FIG. 18A.
Figure 19A:
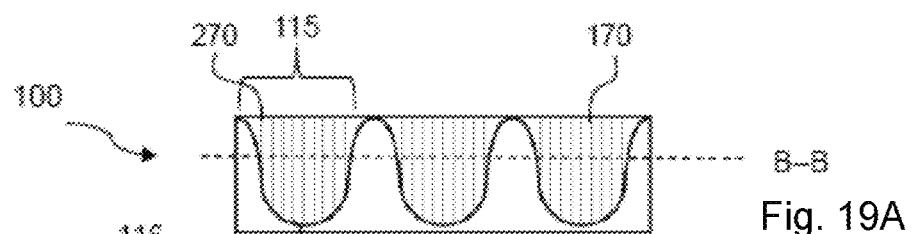
FIG. 19A-C are schematic drawings of another exemplary embodiment of an array of wells 100.

Additional embodiments and geometries are shown in FIGS. 18, 19, and 20. FIG. 17 is a schematic drawing of an exemplary embodiment of an array of wells 100, showing individual wells 115 In the embodiment illustrated in FIG. 17, well 115 has a mouth 101. Mouth 101 is a region at the top part of the well, adjacent the top opening 111 of the well 115, which provides a more open area, before the well constricts to form a well-bottom where cells settle to form spheroids. In embodiments, mouth 101 can be conical (wider at the top of the mouth than at the bottom of the mouth) and annular in shape (as shown in FIG. 17A and FIG. 18A, where the well is round). In additional embodiments, as shown in, for example, FIG. 19A, where the well has a round opening, but is parabolic in shape, mouth 101 may be parabolic.

In some embodiments, well geometries comprise capillary structures (including, for example, a mouth, ridge fissure, rounded or parabolic top opening, etc.) in the well walls to facilitate the escape of air upon introduction of liquid into the well. FIG. 17B is a top-down view, taken at line B-B of FIG. 17A, illustrating a ridge 170. As shown in FIG. 17B, the ridge is a bump or a protuberance from the mouth 101 or the sidewall 113 of the well. In embodiments, the ridge extends the length of the microwell from the top opening 111 to the well bottom 116. In additional embodiments, the ridge extends from the top of the mouth 111 to the bottom of the mouth 112. The sharp angles formed on either side of the ridge 170 create a capillary force on the aqueous fluid to provide for fluid entry to the microwell without air entrapment.

FIG. 18B is a top-down view of an array of wells 100 shown in cross section in FIG. 18A. FIG. 18B illustrates a fissure 270. As shown in FIG. 18B, the fissure is an indentation in the sidewall 113 of the well 115. The sharp angles formed on either side of the fissure 270 create a capillary force to allow aqueous fluid flow into the microwell.

Figure 19B:
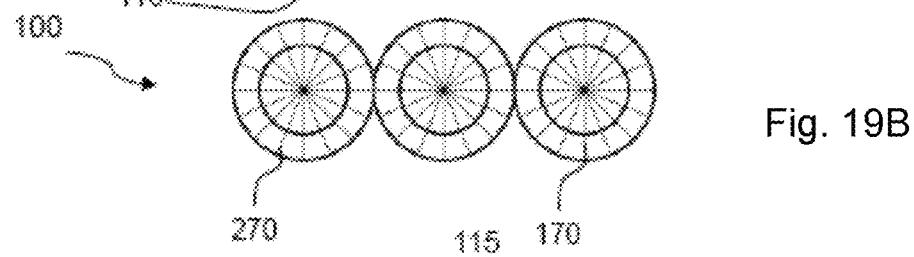

FIGS. 20A and B are schematic drawings of another exemplary embodiment of an array of wells 100. FIG. 19A is an illustration in cross-section. FIG. 19B is a top-down drawing of the exemplary embodiment of an array of wells, taken at line B-B of FIG. 19A. FIGS. 19A and B illustrate that each well 115 may have more than one ridge 170 or fissure 270, and that ridges 170 or fissures 270 may be arranged in an array within the well 115. As shown in FIGS. 19A and B, in embodiments, a radial distribution of ridges and/or fissures is envisioned. The number of capillary structures is not limited to one per microwell. In some embodiments, greater numbers of capillaries increase the rate of fluid entry into the microwell.

Figure 19C:
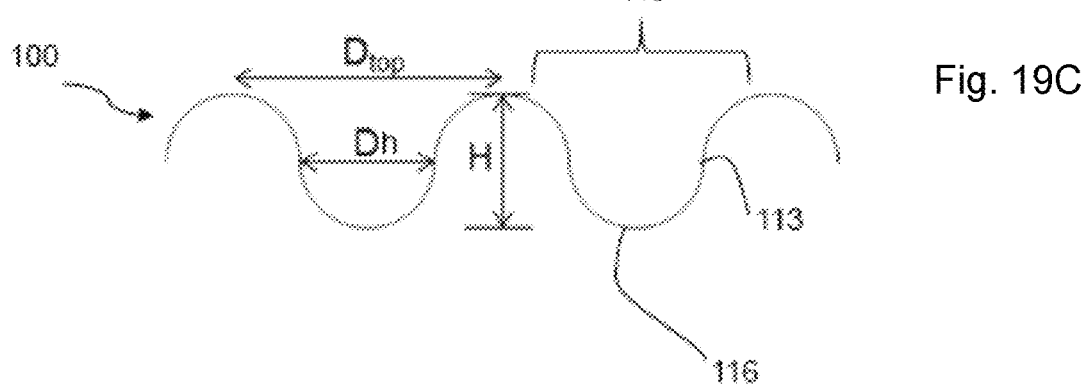

FIG. 19A-C demonstrates inclusion of multiple (e.g., 2, 3, 4, 5, 6, 7, 8, 9, 10, 12, 16, 20, 24, 28, 32, or any ranges therein) vertically-oriented capillary structures within a single well. Features may be regularly-spaced (as depicted in FIG. 19), irregularly spaced, grouped/bunched, etc. In some embodiments, capillary structures extend from the top opening of the well to the well bottom. When multiple capillary structures are present in a single well, the multiple features may be of different types (e.g., ridgelines and/or fissures) and may comprise different shapes (e.g., square, rounded, etc.)

FIG. 19C illustrates that the array of wells 100 may have a sinusoidal or parabolic shape. This shape creates a rounded top edge or well edge which, in embodiments, reduces the entrapment of air at a sharp corner or 90 degree angle at the top of a well. This sinusoidal or parabolic well shape, or rounded top well edge, is also a capillary structure. As shown in FIG. 19C, the well 115 has a top opening having a top diameter $D_{top}$, a height from the bottom of the well 116 to the top of the well H, and a diameter of the well at a height half-way between the top of the well and the bottom 116 of the well $D_{half-way}$.

Both the relative and absolute dimensions of the wells may be selected for the desired culturing conditions. For spheroid growth, the diameter D is preferably one to three times the desired diameter of the 3D cellular aggregate to be cultured in the well. The height H is preferably 0.7 to 1.3 times D. The diameter $D_{top}$ is preferably 1.5 to 2.5 times D. D is preferably 100 micrometers ($\mu$m) to about 2000 micrometers (e.g., 100, 150, 200, 250, 300, 350, 400, 450, 500, 600, 700, 800, 900, 1000, 1200, 1400, 1600, 1800, or 2000 micrometers, including ranges between any two of the foregoing values (e.g., 200-1000 $\mu$m, 200-750 $\mu$m, 300-750 $\mu$m, 400-600 $\mu$m, etc.)). However, alternative relative or absolute dimensions may be employed. For example, D may be from 1 to 10 times (e.g., 2, 3, 4, 5, 6, 7, 8, 9) the desired diameter of the cellular aggregate or any value or range therein between (e.g., 1, 1 to 1.5, 1 to 2, 2, 1 to 2.5, 1 to 3, 2 to 3, 1 to 5, 3 to 5, 2 to 7, etc.). D may be from 100 $\mu$m to 10,000 $\mu$m or any value (e.g., 100, 200, 500, 1000, 2000, 5000) or range therein between (e.g., 100-2000, 200-1000, 300-700, 400-600, 500, etc.). H may be from 0.5 to 10 times D (e.g., 0.5, 0.6, 0.7, 0.8, 0.9, 1, 1.5, 2, 2.5, 3, 4, 5, 6, 7, 8, 9, 10 or any values or ranges therein between). $D_{top}$ may be from 1.1 to 5 times D (e.g., 1.1, 1.2, 1.3, 1.4, 1.5, 1.6, 1.7, 1.8, 1.9, 2, 3, 4, 5 or any values or ranges therein between).

In certain embodiments, the gas permeable cell culture apparatus (e.g., spheroid perfusion bioreactor) of this disclosure permits continuous media replenishment and gas exchange for all of the spheroids on each surface in each culture compartment. In general, media replenishment and gas exchange will also be equivalent, or approximately equivalent, for all the spheroids in each culture compartment. Employing spheroid forming geometry in the wells/compartments, allows the cells added to these bioreactors to form spheroids that are all approximately the same size. Due to the gas permeability of the culture compartments an oxygenator that is typically required for bioreactors will not be required for this system to function optimally.

In certain embodiments, the gas permeable cell culture apparatus allows growing large quantities of cells in a small footprint. For example, a 400 micrometer diameter spheroid may contain an average of 30,000 cells in 3D. In a 2D surface of 400 micrometers in diameter, ~305 cells can attach. So roughly 100 times more cells can be grown in the same unit area in 3D as can be grown in 2D. Growing this many cells in a compact footprint generally requires more nutrients and makes more waste products that need to be removed. The perfusion systems disclosed herein provide such a solution without requiring constant intervention. Moreover, the quality of the cells growing in 3D is generally higher since they function more similarly to cells in vivo.

In certain embodiments, bioreactor chambers/wells can be molded, or thermoformed from gas permeable materials, or constructed from a combination of gas permeable and non-gas permeable materials. Structural support can come in many forms, including, for example, bosses and columns. The chambers/wells may receive fresh medium in parallel through a manifold that distributes equally to all chambers, or the chambers may be fed in series, with the flow reversing from one chamber to the next.

In general, the gas exchange requirements for the cells in the vessel dictate the perfusion rate and by allowing for respiration requirements to be met via gas permeable materials of construction it allows the perfusion rate to be significantly reduced. This allows for reduced shear flow over the spheroids, which makes it easier to retain spheroids within spheroid formation/retention features in the substrates.

In embodiments where the wells are non-adherent to cells, cells cultured in the apparatuses described herein may be harvested by inverting the apparatus to allow gravity to displace the cells from the wells. Alternatively, flow rates of fluid through media flow channels can be increased to dislodge cells from wells as described above.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "structured surface" includes examples having two or more such "structured surfaces" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture apparatuses often refer to directions when the apparatus is oriented for purposes of culturing cells in the apparatus.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a cell culture apparatus comprising a plate defining a structured surface, one or more rails, a top and one or more manifolds include embodiments where a cell culture apparatus consists of a plate defining a structured surface, one or more rails, a top and one or more manifolds and embodiments where a cell culture apparatus consists essentially of a plate defining a structured surface, one or more rails, a top and one or more manifolds.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A cell culture apparatus comprising a plurality of plates stacked on one another, each of said plurality of plates having a first major surface and an opposing second major surface, wherein the first major surface comprises a plurality of microwells, wherein the plurality of microwells has a cross-sectional shape approximating a sine wave; and a plurality of spacers extending from the first major surface, wherein a plurality of cell culture media flow channels are defined between adjacent plates, wherein the plurality of plates are stacked to align spacers of adjacent plates, the aligned spacers defining walls extending from a bottom-most plate to a top-most plate, wherein each of the spacers comprises a plurality of first air channels disposed along the length of the spacer, wherein at least one wall of the walls defines a plurality of second air channels extending from the bottom-most plate to the top-most plate, wherein the second air channels are formed by the aligned spacers aligning the first air channels of the adjacent spacers, wherein the first and second air channels are in gaseous communication with an exterior of the cell culture apparatus and are in gaseous communication with at least one of the plurality of cell culture media flow channels.

2. The cell culture apparatus of claim 1, wherein the plurality of spacers extend from the first major surface along a length of the plate, wherein the plurality of cell culture media flow channels are defined between adjacent spacers above a first major surface of a plate and below an opposing second major surface of an adjacent plate of the plurality of plates.

3. The cell culture apparatus of claim 1, wherein each microwell has an interior surface defining an upper aperture and a nadir, wherein the upper aperture of each well has a diametric dimension in a range from 100 micrometers to 2000 micrometer.

4. The cell culture apparatus according to claim 1, further comprising an inlet and an outlet, wherein each of the plurality of cell culture media flow channels is in fluid communication with the inlet and the outlet.

5. The cell culture apparatus according to claim 4, further comprising an inlet manifold that defines the inlet and defines a plurality of inlet flow channel apertures, wherein each of the plurality of inlet flow channel apertures is in fluid communication with a respective media flow channel.

6. The cell culture apparatus according to claim 4, further comprising an outlet manifold that defines the outlet and defines a plurality of outlet flow channel apertures, wherein each outlet flow channel apertures is in fluid communication with a respective media flow channel.

7. The cell culture apparatus according to claim 1, further comprising a top plate disposed over a top-most cell culture plate of the plurality of stacked plates.

8. The cell culture apparatus according to claim 1, wherein the plurality of microwells comprises an array of hexagonal close-packed wells.

9. The cell culture apparatus according to claim 1, wherein each microwells has a depth defined from an upper aperture to a nadir, wherein the depth is in a range from 200 micrometers to 2000 micrometers.

10. The cell culture apparatus of claim 1, wherein each of the microwells is non-adherent to cells.

11. The cell culture apparatus of claim 1, wherein the plurality of plates is gas permeable via the plurality of microwells.

12. A cell culture system comprising:
a cell culture apparatus according to claim 4; and
an oxygenator coupled to the inlet.

13. The cell culture system of claim 12, further comprising a pump coupled to the inlet.

14. A method comprising:
introducing cells into the plurality of microwells of the cell culture apparatus according to claim 1; and
perfusing a cell culture medium through the cell culture media flow channels of the cell culture apparatus at a first rate to culture the cells in the microwells.

15. The method according to claim 14, further comprising perfusing the cell culture medium through the cell culture media flow channels at a second rate higher than the first rate to remove the cells from the plurality of microwells.

16. A method of producing protein, comprising:
a) culturing cells expressing a protein in the plurality of microwells of the cell culture apparatus according to claim 1; and
b) isolating said protein from said cells.

* * * * *